(12) United States Patent
Zhu et al.

(10) Patent No.: US 8,114,982 B2
(45) Date of Patent: Feb. 14, 2012

(54) MULTI-MICRORNA METHODS AND COMPOSITIONS

(75) Inventors: Liang Zhu, Ardsley, NY (US); Daqian Sun, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 12/312,616

(22) PCT Filed: Nov. 28, 2007

(86) PCT No.: PCT/US2007/024491
§ 371 (c)(1),
(2), (4) Date: Aug. 4, 2009

(87) PCT Pub. No.: WO2008/069940
PCT Pub. Date: Jun. 12, 2008

(65) Prior Publication Data
US 2010/0068814 A1    Mar. 18, 2010

Related U.S. Application Data

(60) Provisional application No. 60/873,180, filed on Dec. 6, 2006.

(51) Int. Cl.
*C07H 21/04*    (2006.01)
(52) U.S. Cl. .................. 536/24.5; 536/24.31; 536/24.1; 514/44

(58) Field of Classification Search .................. None
See application file for complete search history.

(56) References Cited

U.S. PATENT DOCUMENTS

| | | | |
|---|---|---|---|
| 2004/0053411 A1* | 3/2004 | Cullen et al. .................. 435/455 |
| 2005/0197313 A1 | 9/2005 | Roelvink et al. |
| 2005/0214851 A1 | 9/2005 | Arts et al. |
| 2005/0227940 A1 | 10/2005 | Rossi et al. |

OTHER PUBLICATIONS

Yokoi et al. Down-regulation of skp2 induces apoptosis in lung-cancer cells. Cancer Sci 2003, vol. 94:344-349.*
Chung et al. Nucleic Acid Research 2006, vol. 13:1-14.*
The International Search Report as published under WO 2008/069940 A3, for PCT Application No. PCT/US2007/024491.
Cullen "RNAi the natural way." Nature Genetics 37(11):1163-1165, Nov. 2005.
Lee, et al. "Expression of small interfering RNAs targeted against HIV-1 rev transcripts in human cells." Nature Biotechnology 19:500-505, May 2002.

* cited by examiner

*Primary Examiner* — Kimberly Chong
(74) *Attorney, Agent, or Firm* — Amster, Rothstein & Ebenstein LLP

(57) ABSTRACT

Provided are DNAs comprising a polynucleotide that encodes at least a first modified miR-30 precursor and a second modified miR-30 precursor. Also provided are vectors comprising the the DNAs, where the vector can replicate in a host cell. Additionally, specific lentiviral vectors comprising the above-described DNA are provided, as are methods of inhibiting expression of a target gene in a eukaryotic cell.

32 Claims, 9 Drawing Sheets

FIG. 1 (A-C)
A
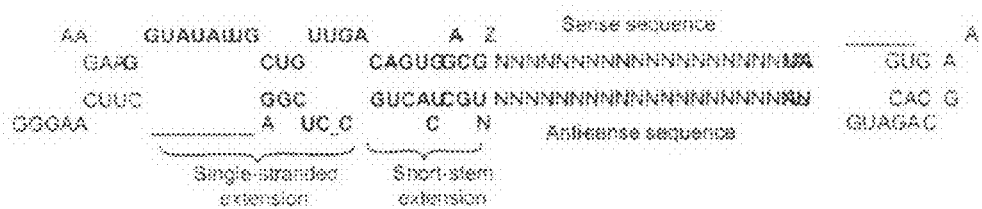
B
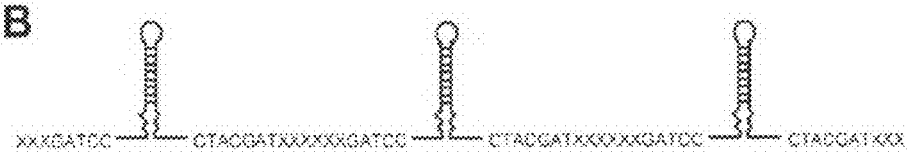
C
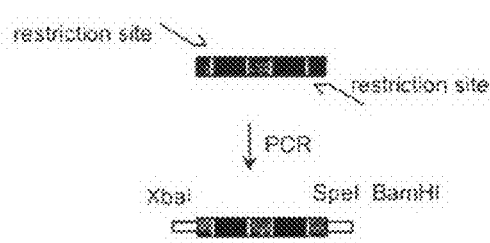

FIG. 1 (D-F)
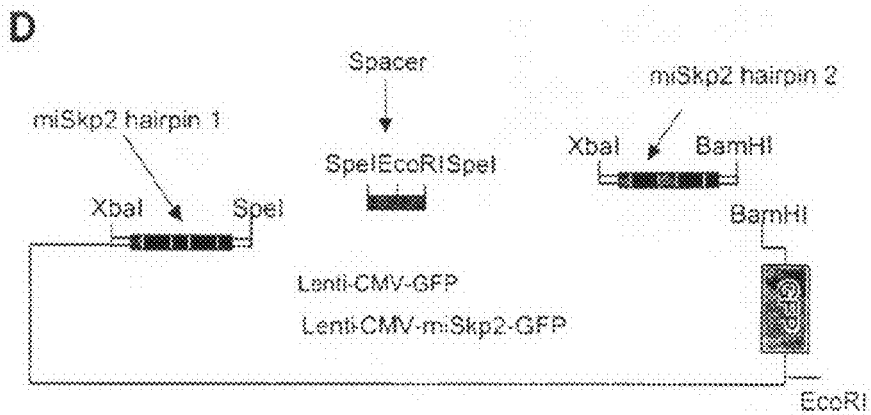
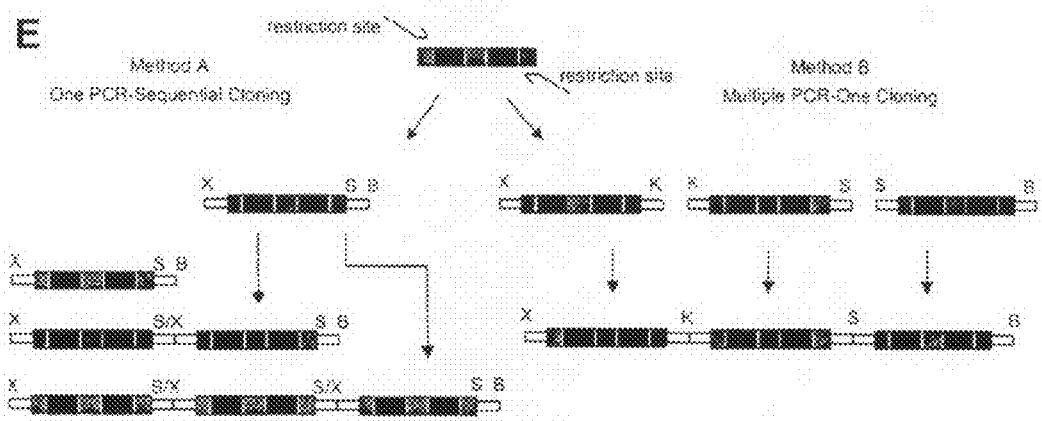
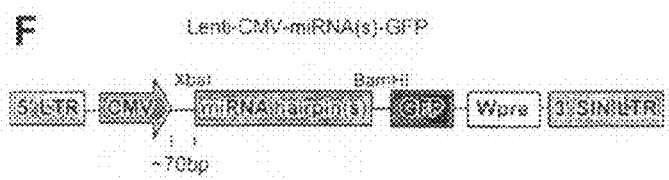

FIG. 4
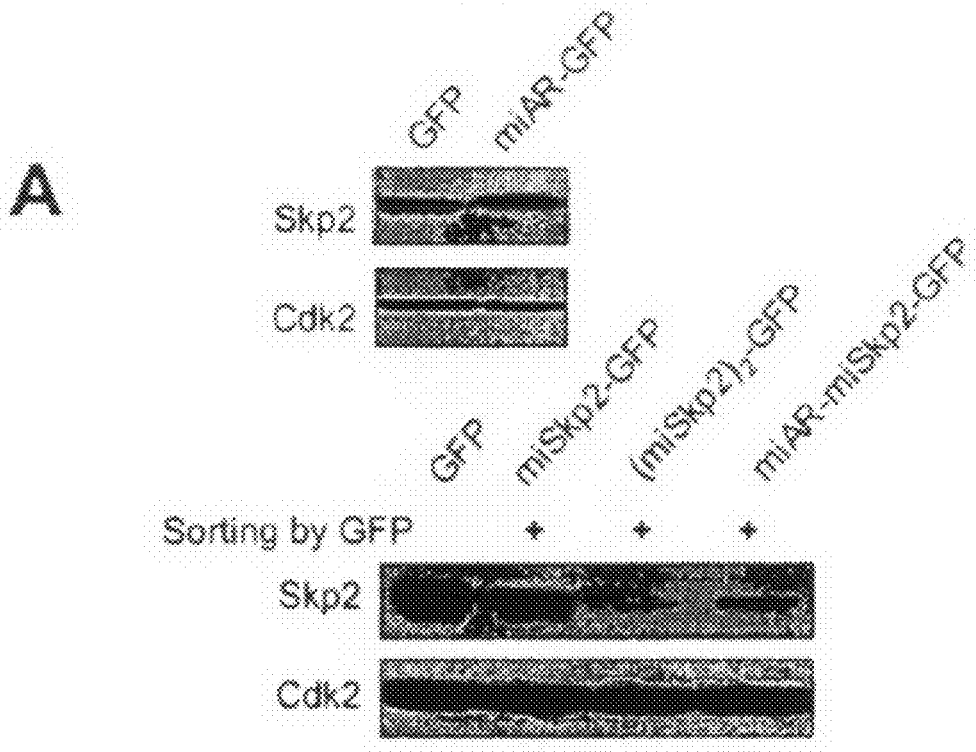
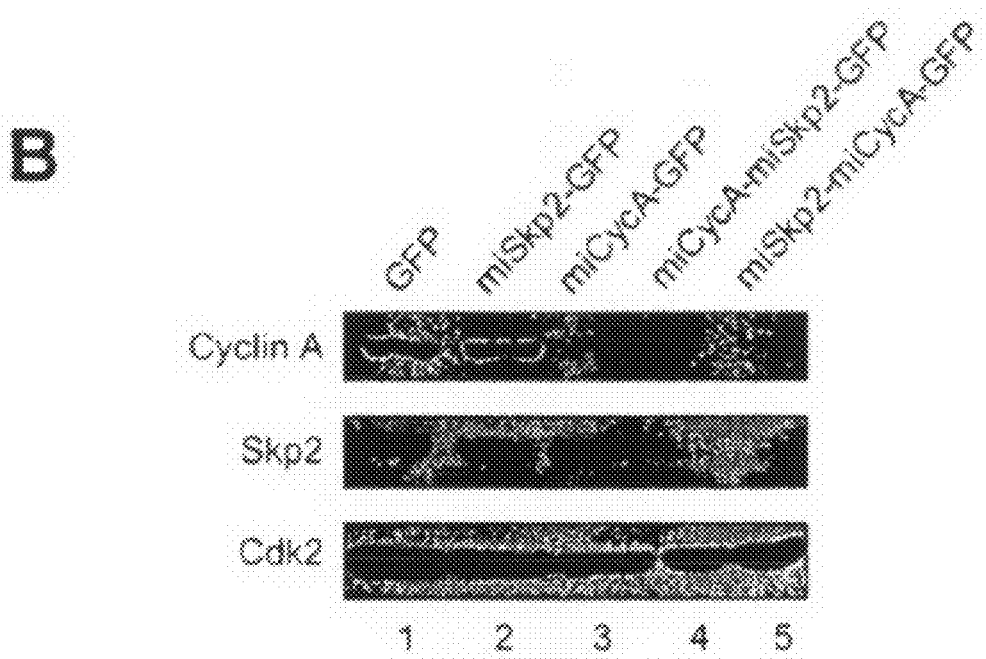

FIG. 8
| Names of hairpins | Artificial sequences between the two hairpins | Spacing Distance | Average GFP values |
|---|---|---|---|
| 1hairpin | | | 297 |
| 2(6)hairpin | ACTAGA | 35.4 Å | 70 |
| 2(13)hairpin | CTACGATACTAGA | 76.7 Å | 60 |
| 2(18)hairpin | CTACGATACTAGAGATCC | 106 Å | 58 |
| 2(25)hairpin | CTACGAT(ACTAGTGAATTC)₁ACTAGA | 148 Å | 60 |
| 2(37)hairpin | CTACGAT(ACTAGTGAATTC)₂ACTAGA | 218 Å | 124 |
| 2(73)hairpin | CTACGAT(ACTAGTGAATTC)₆ACTAGA | 431 Å | 300 |
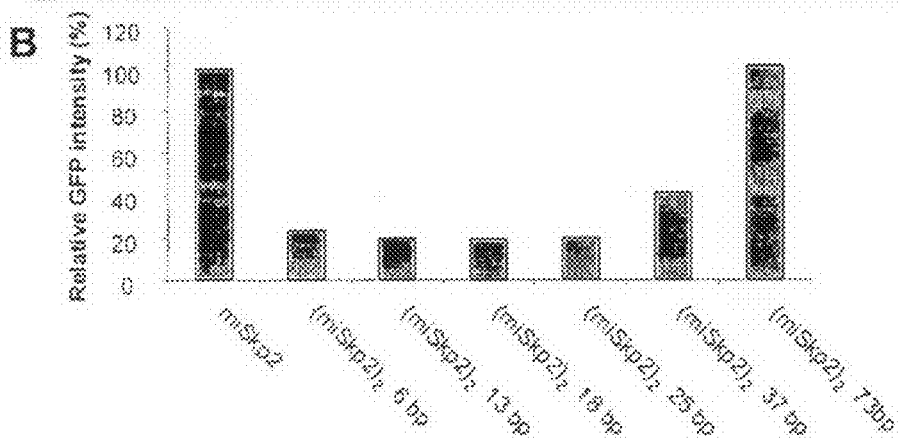
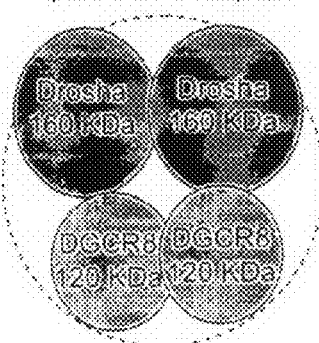

SEQUENCE LISTING

<160> NUMBER OF SEQ ID NOS: 28

<210> SEQ ID NO 1
<211> LENGTH: 89
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (12)..(35)
<223> OTHER INFORMATION: n is a, c, g or u
<220> FEATURE:
<221> NAME/KEY: misc_feature
<222> LOCATION: (53)..(74)
<223> OTHER INFORMATION: n is a, c, g or u

<400> SEQUENCE: 1
gacagugagc gnnnnnnnnn nnnnnnnnnn nnnnngugar rcsmswgakr ugnnnnnnnn    60
nnnnnnnnnn nnnnugccua cugccucgg                                    89

<210> SEQ ID NO 2
<211> LENGTH: 85
<212> TYPE: RNA
<213> ORGANISM: artificial
<220> FEATURE:
<223> OTHER INFORMATION: sequence within modified miR-30
<220> FEATURE:

```
<221> NAME/KEY: misc_feature
<222> LOCATION: (12)..(33)
<223> OTHER INFORMATION: n is a, c, g or u
<220> FEATURE:
<221> NAME/KEY: misc_feature
<222> LOCATION: (51)..(70)
<223> OTHER INFORMATION: n is a, c, g or u

<400> SEQUENCE: 2
gacagugagc gnnnnnnnnn nnnnnnnnnn nnngugarrc smswgakrug nnnnnnnnnn      60
nnnnnnnnnn ugccuacugc cucgg                                           85

<210> SEQ ID NO 3
<211> LENGTH: 118
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (31)..(52)
<223> OTHER INFORMATION: n is a, c, g or u
<220> FEATURE:
<221> NAME/KEY: misc_feature
<222> LOCATION: (72)..(93)
<223> OTHER INFORMATION: n is a, c, g or u

<400> SEQUENCE: 3
aagaagguau auugcuguug acagugagcg nnnnnnnnnn nnnnnnnnnn nnuagugaag      60
ccacagaugu annnnnnnnn nnnnnnnnnn nnnugccuac ugccucggac uucaaggg      118

<210> SEQ ID NO 4
<211> LENGTH: 97
<212> TYPE: DNA
<213> ORGANISM: artificial
<220> FEATURE:
<223> OTHER INFORMATION: Skp2 P183088 PCR template oligonucleotide

<400> SEQUENCE: 4
tgctgttgac agtgagcgaa ccttagacct cacaggtaaa tagtgaagcc acagatgtat      60
ttacctgtga ggtctaaggt ctgcctactg cctcgga                              97

<210> SEQ ID NO 5
<211> LENGTH: 97
<212> TYPE: DNA
<213> ORGANISM: artificial
<220> FEATURE:
<223> OTHER INFORMATION: AR HP140363 PCT template oligonucleotide

<400> SEQUENCE: 5
tgctgttgac agtgagcgac cagcagaaat gattgcacta tagtgaagcc acagatgtat      60
agtgcaatca tttctgctgg ctgcctactg cctcgga                              97

<210> SEQ ID NO 6
<211> LENGTH: 97
<212> TYPE: DNA
<213> ORGANISM: artificial
<220> FEATURE:
<223> OTHER INFORMATION: Cyclin A HP105501 PCT template oligonucleotide

<400> SEQUENCE: 6
tgctgttgac agtgagcgac gttcctcctt ggaaagcaaa tagtgaagcc acagatgtat      60
ttgctttcca aggaggaacg gtgcctactg cctcgga                              97

<210> SEQ ID NO 7
```

```
<211> LENGTH: 44
<212> TYPE: DNA
<213> ORGANISM: artificial
<220> FEATURE:
<223> OTHER INFORMATION: 5' primer for PCR
<220> FEATURE:
<221> NAME/KEY: misc_feature
<222> LOCATION: (4)..(9)
<223> OTHER INFORMATION: n is a, c, g or t

<400> SEQUENCE: 7
gctnnnnnng atccaagaag gtatattgct gttgacagtg agcg           44

<210> SEQ ID NO 8
<211> LENGTH: 41
<212> TYPE: DNA
<213> ORGANISM: artificial
<220> FEATURE:
<223> OTHER INFORMATION: 3' primer for PCR
<220> FEATURE:
<221> NAME/KEY: misc_feature
<222> LOCATION: (4)..(9)
<223> OTHER INFORMATION: n is a, c, g or t

<400> SEQUENCE: 8
ctannnnnna tcgtagccct tgaagtccga ggcagtaggc a              41

<210> SEQ ID NO 9
<211> LENGTH: 19
<212> TYPE: DNA
<213> ORGANISM: artificial
<220> FEATURE:
<223> OTHER INFORMATION: Skp2 target sense hybridization probe

<400> SEQUENCE: 9
ccttagacct cacaggtaa                                       19

<210> SEQ ID NO 10
<211> LENGTH: 19
<212> TYPE: DNA
<213> ORGANISM: artificial
<220> FEATURE:
<223> OTHER INFORMATION: Skp2 target antisense hybridization probe

<400> SEQUENCE: 10
ttacctgtga ggtctaagg                                       19

<210> SEQ ID NO 11
<211> LENGTH: 30
<212> TYPE: DNA
<213> ORGANISM: artificial
<220> FEATURE:
<223> OTHER INFORMATION: U6 antisense hybridization probe

<400> SEQUENCE: 11
gcagggccca tgctaatctt ctctgtatcg                           30

<210> SEQ ID NO 12
<211> LENGTH: 85
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (12)..(35)
<223> OTHER INFORMATION: n is a, c, g or u
<220> FEATURE:
<221> NAME/KEY: misc_feature
<222> LOCATION: (49)..(70)
```

<223> OTHER INFORMATION: n is a, c, g or u

<400> SEQUENCE: 12
gacagugagc gnnnnnnnnn nnnnnnnnnn nnnnacagc gwgakrugnn nnnnnnnnnn    60
nnnnnnnnnn ugccuacugc cucgg                                        85

<210> SEQ ID NO 13
<211> LENGTH: 91
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (12)..(35)
<223> OTHER INFORMATION: n is a, c, g or u
<220> FEATURE:
<221> NAME/KEY: misc_feature
<222> LOCATION: (55)..(76)
<223> OTHER INFORMATION: n is a, c, g or u

<400> SEQUENCE: 13
gacagugagc gnnnnnnnnn nnnnnnnnnn nnnnuagug arrcsmswga krugnnnnn    60 nnnnnnnnnn nnnnnnugcc uacugccucg g                                 91

<210> SEQ ID NO 14
<211> LENGTH: 87
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (12)..(35)
<223> OTHER INFORMATION: n is a, c, g or u
<220> FEATURE:
<221> NAME/KEY: misc_feature
<222> LOCATION: (51)..(72)
<223> OTHER INFORMATION: n is a, c, g or u

<400> SEQUENCE: 14
gacagugagc gnnnnnnnnn nnnnnnnnnn nnnnuaaca gcgwgakrug nnnnnnnnnn    60
nnnnnnnnnn nnugccuacu gccucgg                                      87

<210> SEQ ID NO 15
<211> LENGTH: 93
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (12)..(35)
<223> OTHER INFORMATION: n is a, c, g or u
<220> FEATURE:
<221> NAME/KEY: misc_feature
<222> LOCATION: (57)..(78)
<223> OTHER INFORMATION: n is a, c, g or u

<400> SEQUENCE: 15
gacagugagc gnnnnnnnnn nnnnnnnnnn nnnnuagug arrcsmswga krugugnnnn    60
nnnnnnnnnn nnnnnnnnug ccuacugccu cgg                               93

<210> SEQ ID NO 16
<211> LENGTH: 89
<212> TYPE: RNA
<213> ORGANISM: artificial
<220> FEATURE:

-continued

```
<223> OTHER INFORMATION: sequence within modified miR-30
<220> FEATURE:
<221> NAME/KEY: misc_feature
<222> LOCATION: (12)..(35)
<223> OTHER INFORMATION: n is a, c, g or u
<220> FEATURE:
<221> NAME/KEY: misc_feature
<222> LOCATION: (53)..(74)
<223> OTHER INFORMATION: n is a, c, g or u

<400> SEQUENCE: 16
gacagugagc gnnnnnnnnn nnnnnnnnnn nnnnnuaaca gcgwgakrug ugnnnnnnnn      60
nnnnnnnnnn nnnnugccua cugccucgg                                        89

<210> SEQ ID NO 17
<211> LENGTH: 91
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (12)..(35)
<223> OTHER INFORMATION: n ia a, c, g or u
<220> FEATURE:
<221> NAME/KEY: misc_feature
<222> LOCATION: (55)..(76)
<223> OTHER INFORMATION: n ia a, c, g or u

<400> SEQUENCE: 17
gacagugagc gnnnnnnnnn nnnnnnnnnn nnnnngugar rcsmswgakr ugugnnnnnn      60
nnnnnnnnnn nnnnnnugcc uacugccucg g                                     91

<210> SEQ ID NO 18
<211> LENGTH: 87
<212> TYPE: RNA
<213> ORGANISM: artificial
<220> FEATURE:
<223> OTHER INFORMATION: sequence within modified miR-30
<220> FEATURE:
<221> NAME/KEY: misc_feature
<222> LOCATION: (12)..(35)
<223> OTHER INFORMATION: n is a, c, g or u
<220> FEATURE:
<221> NAME/KEY: misc_feature
<222> LOCATION: (51)..(72)
<223> OTHER INFORMATION: n is a, c, g or u

<400> SEQUENCE: 18
gacagugagc gnnnnnnnnn nnnnnnnnnn nnnnacagc gwgakrugug nnnnnnnnnn       60
nnnnnnnnnn nnugccuacu gccucgg                                          87

<210> SEQ ID NO 19
<211> LENGTH: 129
<212> TYPE: RNA
<213> ORGANISM: artificial
<220> FEATURE:
<223> OTHER INFORMATION: sequence for artificial miRNA hairpin design
<220> FEATURE:
<221> NAME/KEY: misc_feature
<222> LOCATION: (31)..(31)
<223> OTHER INFORMATION: n= any nucleotide that is not a complement to
      the nucleotide at residue 96
<220> FEATURE:
<221> NAME/KEY: misc_feature
<222> LOCATION: (32)..(52)
<223> OTHER INFORMATION: n is a, c, g or u
<220> FEATURE:
<221> NAME/KEY: misc_feature
<222> LOCATION: (75)..(75)
<223> OTHER INFORMATION: n= the nucleotide that is a complement to the
```

```
        nucleotide at residue 52
<220> FEATURE:
<221> NAME/KEY: misc_feature
<222> LOCATION: (76)..(76)
<223> OTHER INFORMATION: n= the nucleotide that is a complement to the
      nucleotide at residue 51
<220> FEATURE:
<221> NAME/KEY: misc_feature
<222> LOCATION: (77)..(77)
<223> OTHER INFORMATION: n= the nucleotide that is a complement to the
      nucleotide at residue 50
<220> FEATURE:
<221> NAME/KEY: misc_feature
<222> LOCATION: (78)..(78)
<223> OTHER INFORMATION: n= the nucleotide that is a complement to the
      nucleotide at residue 49
<220> FEATURE:
<221> NAME/KEY: misc_feature
<222> LOCATION: (79)..(79)
<223> OTHER INFORMATION: n= the nucleotide that is a complement to the
      nucleotide at residue 48
<220> FEATURE:
<221> NAME/KEY: misc_feature
<222> LOCATION: (80)..(80)
<223> OTHER INFORMATION: n= the nucleotide that is a complement to the
      nucleotide at residue 47
<220> FEATURE:
<221> NAME/KEY: misc_feature
<222> LOCATION: (81)..(81)
<223> OTHER INFORMATION: n= the nucleotide that is a complement to the
      nucleotide at residue 46
<220> FEATURE:
<221> NAME/KEY: misc_feature
<222> LOCATION: (82)..(82)
<223> OTHER INFORMATION: n= the nucleotide that is a complement to the
      nucleotide at residue 45
<220> FEATURE:
<221> NAME/KEY: misc_feature
<222> LOCATION: (83)..(83)
<223> OTHER INFORMATION: n= the nucleotide that is a complement to the
      nucleotide at residue 44
<220> FEATURE:
<221> NAME/KEY: misc_feature
<222> LOCATION: (84)..(84)
<223> OTHER INFORMATION: n= the nucleotide that is a complement to the
      nucleotide at residue 43
<220> FEATURE:
<221> NAME/KEY: misc_feature
<222> LOCATION: (85)..(85)
<223> OTHER INFORMATION: n= the nucleotide that is a complement to the
      nucleotide at residue 42
<220> FEATURE:
<221> NAME/KEY: misc_feature
<222> LOCATION: (86)..(86)
<223> OTHER INFORMATION: n= the nucleotide that is a complement to the
      nucleotide at residue 41
<220> FEATURE:
<221> NAME/KEY: misc_feature
<222> LOCATION: (87)..(87)
<223> OTHER INFORMATION: n= the nucleotide that is a complement to the
      nucleotide at residue 40
<220> FEATURE:
<221> NAME/KEY: misc_feature
<222> LOCATION: (88)..(88)
<223> OTHER INFORMATION: n= the nucleotide that is a complement to the
      nucleotide at residue 39
<220> FEATURE:
<221> NAME/KEY: misc_feature
<222> LOCATION: (89)..(89)
<223> OTHER INFORMATION: n= the nucleotide that is a complement to the
      nucleotide at residue 38
<220> FEATURE:
<221> NAME/KEY: misc_feature
<222> LOCATION: (90)..(90)
<223> OTHER INFORMATION: n= the nucleotide that is a complement to the
      nucleotide at residue 37
<220> FEATURE:
<221> NAME/KEY: misc_feature
<222> LOCATION: (91)..(91)
<223> OTHER INFORMATION: n= the nucleotide that is a complement to the
```

```
      nucleotide at residue 36
<220> FEATURE:
<221> NAME/KEY: misc_feature
<222> LOCATION: (92)..(92)
<223> OTHER INFORMATION: n= the nucleotide that is a complement to the
      nucleotide at residue 35
<220> FEATURE:
<221> NAME/KEY: misc_feature
<222> LOCATION: (93)..(93)
<223> OTHER INFORMATION: n= the nucleotide that is a complement to the
      nucleotide at residue 34
<220> FEATURE:
<221> NAME/KEY: misc_feature
<222> LOCATION: (94)..(94)
<223> OTHER INFORMATION: n= the nucleotide that is a complement to the
      nucleotide at residue 33
<220> FEATURE:
<221> NAME/KEY: misc_feature
<222> LOCATION: (95)..(95)
<223> OTHER INFORMATION: n= the nucleotide that is a complement to the
      nucleotide at residue 32
<220> FEATURE:
<221> NAME/KEY: misc_feature
<222> LOCATION: (96)..(96)
<223> OTHER INFORMATION: n is a,c, g or u
<220> FEATURE:
<221> NAME/KEY: misc_feature
<222> LOCATION: (107)..(107)
<223> OTHER INFORMATION: n is a, c, g or u

<400> SEQUENCE: 19
aagaagguau auugcuguug acagugagcg nnnnnnnnnn nnnnnnnnnn nndbvdvgug        60
aagccacaga aguannnnnn nnnnnnnnnn nnnnnnugcc uacugcncuc ggadbvbvbb       120
cuucaaggg                                                              129

<210> SEQ ID NO 20
<211> LENGTH: 8
<212> TYPE: DNA
<213> ORGANISM: artificial
<220> FEATURE:
<223> OTHER INFORMATION: 5' sequence of sequence consisting of 3 hairpin
      structures
<220> FEATURE:
<221> NAME/KEY: misc_feature
<222> LOCATION: (1)..(3)
<223> OTHER INFORMATION: n is a, c, g or t

<400> SEQUENCE: 20 nnngatcc                                                                 8

<210> SEQ ID NO 21
<211> LENGTH: 18
<212> TYPE: DNA
<213> ORGANISM: artificial
<220> FEATURE:
<223> OTHER INFORMATION: sequence between hairpins 1 and 2 and hairpins
      2 and 3 of sequence consisting of 3 hairpin structures
<220> FEATURE:
<221> NAME/KEY: misc_feature
<222> LOCATION: (8)..(13)
<223> OTHER INFORMATION: n is a, c, g or t

<400> SEQUENCE: 21
ctacgatnnn nnngatcc                                                     18

<210> SEQ ID NO 22
<211> LENGTH: 10
<212> TYPE: DNA
<213> ORGANISM: artificial
<220> FEATURE:
<223> OTHER INFORMATION: 3' sequence of sequence consisting of 3 hairpin
      structures
```

```
<220> FEATURE:
<221> NAME/KEY: misc_feature
<222> LOCATION: (8)..(10)
<223> OTHER INFORMATION: n is a, c, g or t

<400> SEQUENCE: 22 ctacgatnnn                                                              10

<210> SEQ ID NO 23
<211> LENGTH: 6
<212> TYPE: DNA
<213> ORGANISM: artificial
<220> FEATURE:
<223> OTHER INFORMATION: Sequence between two hairpin structures

<400> SEQUENCE: 23 actaga                                                                   6

<210> SEQ ID NO 24
<211> LENGTH: 13
<212> TYPE: DNA
<213> ORGANISM: artificial
<220> FEATURE:
<223> OTHER INFORMATION: Sequence between two hairpin structures

<400> SEQUENCE: 24
ctacgatact aga                                                          13

<210> SEQ ID NO 25
<211> LENGTH: 18
<212> TYPE: DNA
<213> ORGANISM: artificial
<220> FEATURE:
<223> OTHER INFORMATION: Sequence between two hairpin structures

<400> SEQUENCE: 25
ctacgatact agagatcc                                                     18

<210> SEQ ID NO 26
<211> LENGTH: 25
<212> TYPE: DNA
<213> ORGANISM: artificial
<220> FEATURE:
<223> OTHER INFORMATION: Sequence between two hairpin structures

<400> SEQUENCE: 26
ctacgatact agtgaattca ctaga                                             25

<210> SEQ ID NO 27
<211> LENGTH: 37
<212> TYPE: DNA
<213> ORGANISM: artificial
<220> FEATURE:
<223> OTHER INFORMATION: Sequence between two hairpin structures

<400> SEQUENCE: 27
ctacgatact agtgaattca ctagtgaatt cactaga                                37

<210> SEQ ID NO 28
<211> LENGTH: 73
<212> TYPE: DNA
<213> ORGANISM: artificial
<220> FEATURE:
<223> OTHER INFORMATION: Sequence between two hairpin structures
```

```
<400> SEQUENCE: 28
ctacgatact agtgaattca ctagtgaatt cactagtgaa ttcactagtg aattcactag    60
tgaattcact aga                                                       73
```

MULTI-MICRORNA METHODS AND COMPOSITIONS

This is a U.S. national phase of PCT Application No. PCT/US2007/024491, filed Nov. 28, 2007, which claims the benefit of U.S. Provisional Application No. 60/873,180, filed Dec. 6, 2006.

STATEMENT REGARDING FEDERALLY SPONSORED RESEARCH OR DEVELOPMENT

This invention was made with government support under Grant Nos. R01CA87566 and R01DK58640 awarded by the National Institutes of Health. The government has certain rights in the invention.

BACKGROUND OF THE INVENTION (1) Field of the Invention

The present invention generally relates to miRNA vectors. More specifically, the invention is directed to vectors having more than one miR-30 hairpin that can be expressed by RNA polymerase II.

(2) Description of the Related Art

A recent advance in gene silencing methodology is to modify the stem sequence of miR-30 microRNA (miRNA) hairpin to achieve knockdown (i.e., reduction of expression) of artificially targeted genes (Zeng el al., 2002; McManus et al., 2002; Boden et al., 2004; Zhou et al., 2005; Stegmeier et al., 2005; Silva et al., 2005; Dickins et al., 2005). Modified miR-30 can achieve more effective knockdown than previous short-hairpin RNA (shRNA)-based methods (Boden et al., 2004; Silva et al., 2005) and can be expressed from pol II promoters. Nevertheless, knockdown efficiencies vary for different target genes or with different ways of expressing the modified miR-30, especially when knockdown vectors are present in low numbers in target cells (Stegmeier et al., 2005; Silva et al., 2005; Dickins et al., 2005). Inadequate efficiencies of gene knockdown for various research and therapeutic purposes remain frequently encountered.

For microRNA mediated gene silencing, one potential means to improve gene silencing efficiency is to express multiple copies of the microRNA hairpin from a single transcript. This concept originated from the finding that microRNA hairpins are often processed from within larger RNA polymerase II (pol II) transcripts (Kim, 2005). Since primary pol II transcripts can encode multiple genes (polycistronic), it was presumed that multiple hairpins could also be processed out of one pol II transcript. In nature, closely clustered microRNA hairpins have been found in the genome of many species, including man (refs. and figure XX), suggesting that multiple microRNA hairpins could be processed from one transcript. Artificial constructs expressing more than one microRNA hairpin have been made, with variable results (Zhou et al., 2005; Chung et al., 2006; PCT Publication No. WO 2006/044322 A2).

SUMMARY OF THE INVENTION

The present invention is based in part on the development and optimization of DNA constructs that encode more than one mil-30 precursor, allowing expression of both miR-30 hairpins and knockdown of the targeted gene.

The invention is directed to isolated DNAs comprising a polynucleotide that encodes at least a first modified miR-30 precursor and a second modified miR-30 precursor. The first and second modified miR-30 precursors are each at least 80 nucleotides long and comprise a stem-loop structure. The first modified miR-30 precursor further comprises a first miRNA sequence of 20-22 nucleotides on the stem of the stem-loop structure complementary to a portion of a first target sequence, where the first target sequence is a first naturally occurring mRNA sequence. Also, the second-modified miR-30 precursor further comprises a second miRNA sequence of 20-22 nucleotides on the stem-loop structure complementary to a second target sequence, and the first and second modified miR-30 precursors each independently further comprises a sequence complementary to the first and second miRNA sequence, respectively, that base-pairs to the miRNA sequence in the miR-30 precursor in the stem of the stem-loop structure.

The invention is also directed to vectors comprising the above-described DNAs, where the vector can replicate in a host cell.

Additionally, the invention is directed to lentiviral vectors comprising the above-described DNA where the first and second modified miR-30 precursors are each about 118 nucleotides long; the first modified-miR-30 precursor and the second modified miR-30 precursor are about 18 nucleotide's apart; the isolated DNA further comprises a site for a restriction endonuclease between the first modified miR-30 precursor and the second modified miR-30 precursor; the isolated DNA further comprises a gene encoding a encodes a green fluorescent protein (GFP); and the isolated DNA further comprises a promoter operably linked to the isolated DNA such that, when introduced into a eukaryotic cell, the first miR-30 precursor is transcribed and processed into the first miRNA and the second miR-30 precursor is transcribed and processed into the second miRNA, wherein the promoter is a cytomegalovirus promoter.

The invention is further directed to methods of inhibiting expression of a target gene in a eukaryotic cell. The methods comprise introducing into the cell a DNA comprising a polynucleotide that encodes at least a first modified miR-30 precursor and a second modified miR-30 precursor, where the first and second modified miR-30 precursors are each at least 80 nucleotides long and comprise a stem-loop structure; where the first modified miR-30 precursor further comprises a first miRNA sequence of 20-22 nucleotides on the stem of the stem-loop structure complementary to a portion of a first target sequence, wherein the first target sequence is the mRNA of the target gene; where the second modified miR-30 precursor further comprises a second miRNA sequence of 20-22 nucleotides on the stem-loop structure complementary to a second target sequence; where the first and second modified miR-30 precursors each independently further comprises a sequence complementary to the first and second miRNA sequence, respectively, that base-pairs to the miRNA sequence in the miR-30 precursor in the stem of the stem-loop structure; and where the DNA further comprises a promoter operably linked to the DNA such that, when the DNA is introduced into the eukaryotic cell, the first miR-30 precursor is transcribed and processed into the first miRNA and the second miR-30 precursor is transcribed and processed into the second miRNA.

BRIEF DESCRIPTION OF THE DRAWINGS

FIG. 1 is diagrams showing an artificial multi-microRNA (miRNA) hairpin design. Panel A shows the sequence of the 118-nucleotide (nt) modified miR-30 hairpin unit. Folding is based on rna.tbi.univie.ac.at. Artificial sequences are based on Paddison et al., 2004. Ns represent an artificial 22-nt antisense sequence that can be inserted to target a gene of choice. The Z indicates that it does not base pair with the N nucleotide on the opposite strand to preserve the feature of natural miR-30 at this position. UA is an artificial sequence that may destabilize the 5' end of the antisense strand to favor its incorporation into the RNA-induced silencing complex (RISC). Panel B shows artificial sequences linking multiple hairpins. "XXXXXX" accommodates various restriction enzyme sites. Panel C shows the PCR strategy to generate the hairpin units. Panel D shows how multiple fragments are ligated into various two-hairpin constructs that were finally cloned into the XbaI and BamHI sites of Lenti-CMV-GFP vector to obtain Lenti-CMV-miRNA(s)-GFP (Panel F). Panel E shows two cloning protocols for generating multi-miRNA hairpin clusters. Sequences of PCR template and primers are listed in Table 1. Abbreviations for restriction sites are X (XbaI), S (SpeI), B (BamHI), K (KpnI). Presented is a three-hairpin construct for the purpose of illustrating the multi-hairpin design. The actual number of hairpins can vary by individual users according to their needs. Panel F is a representation of a lenti-CMV-miRNAs-GFP vector.

FIG. 4 is photographs of blots showing the knockdown effects of individual hairpins in two-hairpin constructs. Panel A shows a analysis of 293T cells infected by the indicated viruses either at >95% efficiency for western blot (top blots) or at approximately 30% efficiency and green fluorescent protein (GFP) positive cells were isolated by flow cytometry for western blotting (bottom blots). Panel B shows an analsyis of 293T cells, which were infected with the indicated viruses at >95% efficiency and subjected to western blot.

FIG. 8, Panel A shows the artificial sequences between the two hairpins in the miRNA-GFP construct analysis. Panel B is a graph of the relative GFP intensity from the flow cytometry analysis shown in FIG. 7. Panel C is a diagram of the Drosha/DGCR8 complex.

DETAILED DESCRIPTION OF THE INVENTION

Figure 2:
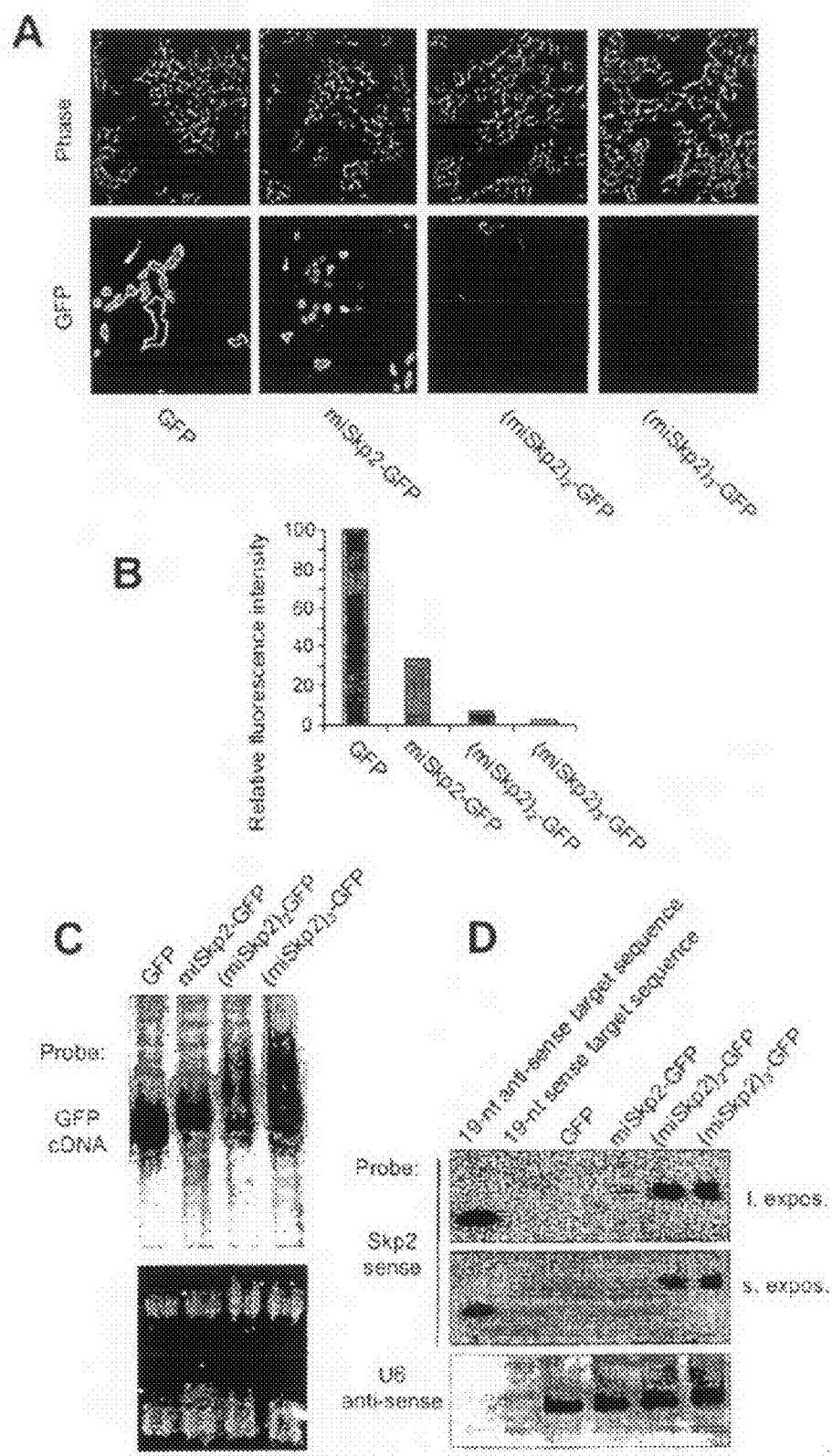
FIG. 2 is micrographs, a graph and photographs of blots and a gel showing the reduction of green fluorescent protein (GFP) expression and increase in production of mature small RNAs by an invention multi-hairpin design. Panel A shows phase and GFP fluorescence micrographs of 293T cells infected at about 30% efficiency by the indicated viruses. Identical exposures were used for GFP pictures. Panel B is a graph of the relative median GFP fluorescence intensity of GFP positive cells shown in panel A as determined by flow cytometry. Panel C shows a northern blot analysis of total RNA extracted from cells transduced with the indicated lentivirus and sorted for GFP positivity. The membrane was probed with GFP cDNA probe (top). Before transfer, the gel was stained with ethidium bromide and photographed (bottom). Panel D shows a northern blot analysis of the same total RNAs used in panel C. Nineteen-nucleotide (nt) oligonucleotides of the Skp2 target sequence (antisense and sense) were used as control and size marker. The membrane was probed with an end-labeled 19-nt oligonucleotide of the Skp2 target sequence (sense) and an U6 antisense oligonucleotide.

The present invention is based in part on the development and optimization of DNA constructs that encode more than one miR-30 precursor on a single RNA polymerase II transcript, allowing expression of both miR-30 hairpins and knockdown of the targeted gene(s). When both precursors are to the same target, knockdown of that target gene is superior to constructs having only one precursor. See Examples.

The invention is directed to DNAs comprising a polynucleotide that encodes at least a first modified miR-30 precursor and a second modified miR-30 precursor. The first and second modified miR-30 precursors are each at least 80 nucleotides long and comprise a stem-loop structure. The first modified miR-30 precursor further comprises a first miRNA sequence of 20-22 nucleotides on the stem of the stem-loop structure complementary to a portion of a first target sequence, where the first target sequence is a first naturally occurring mRNA sequence. Also, the second modified miR-30 precursor further comprises a second miRNA sequence of 20-22 nucleotides on the stem-loop structure complementary to a second target sequence, and the first and second modified miR-30 precursors each independently further comprises a sequence complementary to the first and second miRNA sequence, respectively, that base-pairs to the miRNA sequence in the miR-30 precursor in the stem of the stem-loop structure.

As used herein, an "miR-30 precursor", also called an miR-30 hairpin, is a precursor of the human microRNA miR-30, as it is understood in the literature (e.g., Zeng and Cullen, 2003; Zeng and Cullen, 2005; Zeng et al., 2005; United States Patent Application Publication No. US 2004/0053411 A1), where the precursor could be modified from the wild-type miR-30 precursor in any manner described or implied by that literature, while retaining the ability to be processed into an miRNA.

In these invention DNAs, the first target sequence can be the same as the second target sequence. The first target sequence and the second target sequence can also be on the same mRNA. Alternatively, the first target sequence and the second target sequence can be on different mRNAs. It is also contemplated that, with some of these DNAs, the second target sequence does not naturally occur in the same species as the first target sequence. Alternatively, the second target sequence can naturally occur in the same species as the first target sequence.

Preferably, the modified miR-30 comprises the sequence GACAGUGAGCGNN $(N_{20-22})$ {UA}[GUGA(A/G)(G/A)C (C/G)(A/C)(C/G) or ACAGCG)](A/U)GA(U/G)(G/A) UG{UG} $(N_{20-22})$ UGCCUACUGC CUCGG, where curly brackets indicate optional ribonucleotides; square brackets delineate alternative sequences; (X/Y)=either X or Y at that position; $N(a)_{20-22}$ and $N(b)_{22}$=20-22 nucleotides complementary to target sequence, where the (a) sequence and the (b)

sequence base pair to each other in the stem of the hairpin. More preferably, the modified miR-30 comprises SEQ ID NO:1. Even more preferably, the modified miR-30 comprises SEQ ID NO:2. Most preferably, the modified miR-30 comprises SEQ ID NO:3.

The "target sequences" targeted by the miRNAs in these DNAs are not limited to any particular RNA targets. Where the target is mRNA, the target sequence can be in an intron or an exon of the gene therein, or a sequence upstream or downstream from the coding sequence.

Examples of useful target sequences include sequence from a pathogen, where the invention DNA could be used to prevent or light an infection by the pathogen. Thus, in some invention DNAs, the first target sequence and/or the second target sequence is complementary to an mRNA from a mammalian pathogen. Preferably, the mammalian pathogen is a human pathogen. Preferred mammalian pathogens include viruses.

Other examples of useful target sequences include sequences from a mammal, where the invention DNA can be used to reduce expression of, e.g., regulatory proteins. Thus, some invention DNAs are complementary to a mammalian mRNA. Preferably, the mammalian mRNA is a human mRNA. More preferably, the mammalian mRNA encodes an enzyme. Preferred enzymes here include kinase and phosphatases. A preferred such enzyme is a skp2 protein. Other useful mammalian mRNA targets include receptors.

The first and second modified precursors can be any length that allows transcription and processing of the precursors into miRNA. In some instances, the first and second modified miR-30 precursors are each at least 85 nucleotides long. In other instances, the first and second modified miR-30 precursors are each at least 90 nucleotides long. The first and second modified miR-30 precursors can also each be at least 100 nucleotides long. Preferably, the first and second modified miR-30 precursors are each 80-150 nucleotides long. More preferably, the first and second modified miR-30 precursors are each 90-130 nucleotides long. Most preferably, the first and second modified miR-30 precursors are each about 118 nucleotides long.

As disclosed in Example 2, the distance between the two miR-30 precursors affects the amount that the miR-30 precursors are processed into miRNA. For example, the first modified miR-30 precursor and the second modified miR-30 precursor can be 6-73 nucleotides apart. Preferably, the first modified miR-30 precursor and the second modified miR-30 precursor are 10-50 nucleotides apart. More preferably, the first modified miR-30 precursor and the second modified miR-30 precursor are 13-25 nucleotides apart. Most preferably, the first modified miR-30 precursor and the second modified miR-30 precursor are about 18 nucleotides apart.

Preferably, the invention DNA further comprises a site for a restriction endonuclease between the first modified miR-30 precursor and the second modified miR-30 precursor.

Also, it is preferred if the DNA further comprises a promoter operably linked to the isolated DNA such that, when introduced into a eukaryotic cell, the first miR-30 precursor is transcribed and processed into the first miRNA and the second miR-30 precursor is transcribed and processed into the second miRNA. While the invention DNA is not limited to any particular promoter, the promoter is preferably a mammalian promoter. More preferably, the promoter functions in a human. The promoter is also preferably a viral promoter. The promoter may be a constitutive promoter. Alternatively, the promoter is inducible. Most preferably, the promoter is a cytomegalovirus promoter.

Preferably, with the DNA having a promoter described above, expression of a polypeptide encoded by the first naturally occurring mRNA sequence is reduced in the eukaryotic cell after the isolated DNA is introduced into the eukaryotic cell.

In some uses of the invention DNAs, it is useful for the practitioner to be able to identify the presence, and/or the processing of the transcribed precursor. With those uses, the invention DNA can further comprise a gene encoding a detectable moiety. The DNAs are not narrowly limited to any particular detectable moiety. The skilled artisan could be expected to employ any particular useful detectable moiety without undue experimentation. Preferably, the gene encoding a detectable moiety encodes a green fluorescent protein (GFP). Any other genes can also be present on the invention DNAs as would be useful for, e.g., therapeutic or research purposes. An example is a gene encoding a drug resistance marker, or a gene encoding a therapeutic compound (e.g., a cytokine, or an enzyme missing in the patient).

The invention DNAs can comprise any number of modified miR-30 precursors. Thus, some of the invention DNAs further comprise a third modified miR-30 precursor where the third modified miR-30 precursor comprises a third miRNA sequence of 20-22 nucleotides on the stem-loop structure complementary to a third target sequence, where the third modified miR-30 precursor further comprises a sequence complementary to the third miRNA sequence that base-pairs to the third miRNA sequence in the third miR-30 precursor in the stem of the stem-loop structure. Other invention DNAs further comprise a fourth modified miR-30 precursor where the fourth modified miR-30 precursor comprises a fourth miRNA sequence of 20-22 nucleotides on the stem-loop structure complementary to a fourth target sequence, wherein the fourth modified miR-30 precursor further comprises a sequence complementary to the fourth miRNA sequence that base-pairs to the third miRNA sequence in the third miR-30 precursor in the stem of the stem-loop structure. Invention DNAs comprising a fifth, sixth, seventh, etc modified precursors are also specifically contemplated.

In one of the most preferred invention DNAs, the first and second modified miR-30 precursors are each about 118 nucleotides long; the first modified miR-30 precursor and the second modified miR-30 precursor are about 18 nucleotides apart; the DNA further comprises a site for a restriction endonuclease between the first modified miR-30 precursor and the second modified miR-30 precursor; the DNA further comprises a gene encoding a encodes a green fluorescent protein (GFP); and the DNA further comprises a promoter operably linked to the isolated DNA such that, when introduced into a eukaryotic cell, the first miR-30 precursor is transcribed and processed into the first miRNA and the second miR-30 precursor is transcribed and processed into the second miRNA, where the promoter is a cytomegalovirus promoter. Preferably here, the first target sequence and/or the second target sequence is complementary to a mammalian mRNA encoding a skp2 protein.

The invention DNAs can be in an isolated and purified state, e.g., as appropriate for molecular biological manipulations. Alternatively, the DNA can be transfected into a mammalian cell. The mammalian cell can be in vitro, e.g., in culture or as part of an excised tissue. After transfection, the cell can be transplanted into a living mammal using any known ex vivo protocol. The mammalian cell can also be part of a living mammal, where the cell is transfected in vivo.

The invention is also directed to eukaryotic cells comprising any of the above-described invention DNAs that comprises a promoter. The eukaryotic cells can be any such cell that is known, including any known animal, plant, fungal or protest cell. Preferably, the cells are mammalian cells, more preferably human cells.

Additionally, the invention is directed to vectors comprising any of the above DNAs that comprise a promoter. Preferably, the vector can replicate in a host cell. The host cell can be a prokaryote, e.g., E. coli used to replicate the vector. The host cell can also be a mammalian cell, e.g., a cell having the target sequence. Preferably, the vector is a viral vector, most preferably a lentiviral vector. The invention is also directed to vectors comprising any of these DNAs, in the host cell.

A preferred vector of the invention is a lentiviral vector comprising the above isolated DNA where the first and second modified miR-30 precursors are each about 118 nucleotides long; the first modified miR-30 precursor and the second modified miR-30 precursor are about 18 nucleotides apart; the DNA further comprises a site for a restriction endonuclease between the first modified miR-30 precursor and the second modified miR-30 precursor; the DNA further comprises a gene encoding a encodes a green fluorescent protein (GFP); and the DNA further comprises a promoter operably linked to the isolated DNA such that, when introduced into a eukaryotic cell, the first miR-30 precursor is transcribed and processed into the first miRNA and the second miR-30 precursor is transcribed and processed into the second miRNA, wherein the promoter is a cytomegalovirus promoter. Mammalian cells transfected with that lentiviral vector are also contemplated as within the scope of the invention. Without being bound by any particular mechanism, it is expected that the first miR-30 precursor and the second miR-30 precursor are transcribed together.

The invention is further directed to methods of inhibiting expression of a target gene in a eukaryotic cell. The methods comprise introducing into the cell a DNA comprising a polynucleotide that encodes at least a first modified miR-30 precursor and a second modified miR-30 precursor, where the first and second modified miR-30 precursors are each at least 80 nucleotides long and comprise a stem-loop structure; where the first modified miR-30 precursor further comprises a first miRNA sequence of 20-22 nucleotides on the stem of the stem-loop structure complementary to a portion of a first target sequence, wherein the first target sequence is the mRNA of the target gene; where the second modified miR-30 precursor further comprises a second miRNA sequence of 20-22 nucleotides on the stem-loop structure complementary to a second target sequence; where the first and second modified miR-30 precursors each independently further comprises a sequence complementary to the first and second miRNA sequence, respectively, that base-pairs to the miRNA sequence in the miR-30 precursor in the stem of the stem-loop structure; and where the DNA further comprises a promoter operably linked to the DNA such that, when the DNA is introduced into the eukaryotic cell, the first miR-30 precursor is transcribed and processed into the first miRNA and the second miR-30 precursor is transcribed and processed into the second miRNA.

With some of these methods, the second miRNA sequence is the same as the first miRNA sequence. Alternatively, the second miRNA sequence is complementary to the mRNA of the gene. Either of these methods are preferred in instances where strong inhibition of translation the target gene is desired, since the two miRNA directed to the target gene provides greater inhibition than one.

In other of these methods the eukaryotic cell cannot synthesize the second target sequence. As discussed Example 1 below, greater inhibition of translation of the first target gene is achieved even when the second miRNA is directed to a target sequence that is not in the cell, i.e., an irrelevant miRNA.

The DNA is preferably introduced (i.e., transfected) into the cell as part of a vector that can replicate in a host cell. Any known vector can be used here, including any plasmid or viral vector known in the art. The selection of the appropriate vector for any particular purpose is within the skill of the art.

A preferred vector is a lentiviral vector. More preferably, the first and second modified miR-30 precursors are each about 118 nucleotides long; the first modified miR-30 precursor and the second modified miR-30 precursor are about 18 nucleotides apart; the isolated DNA further comprises a site for a restriction endonuclease between the first modified miR-30 precursor and the second modified miR-30 precursor; the promoter is a cytomegalovirus promoter, and the isolated DNA further comprises a gene encoding a encodes a green fluorescent protein (GFP). Examples of such vectors are described in the examples below:

In some of these methods, the eukaryotic cell is a mammalian cell, preferably a human cell. More preferably, the mammalian cell is part of a living mammal. Most preferably, the mammal is a human.

The "target sequences" targeted by the miRNAs in these methods are not limited to any particular RNA targets. Where the target is mRNA, the target sequence can be in an intron or an exon of the gene therein, or a sequence upstream or downstream from the coding sequence.

Examples of useful target sequences include sequence from a pathogen, where the invention DNA could be used to prevent or fight an infection by the pathogen. Thus, in some invention DNAs; the first target sequence and/or the second target sequence is complementary to an mRNA from a mammalian pathogen. Preferably, the mammalian pathogen is a human pathogen. Preferred mammalian pathogens include, viruses.

Other examples of useful target sequences include sequences from a mammal, where the invention DNA can be used to reduce expression of, e.g., regulatory proteins. Thus, some invention DNAs are complementary to a mammalian mRNA. Preferably, the mammalian mRNA is a human mRNA. More preferably, the mammalian mRNA encodes an enzyme. Preferred enzymes here include kinase and phosphatases. A preferred such enzyme is a skp2 protein. Other useful mammalian mRNA targets include receptors.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

EXAMPLE 1

Multi-miRNA Hairpin Method that Improves Gene Knockdown Efficiency and Provides Linked Multi-Gene Knockdown Example Summary A number of natural microRNA (miRNA) hairpins have been found in clusters of multiple identical or different copies, suggesting that effects of miRNAs can be enhanced and multiple genes can be regulated together by encoding multiple miRNA hairpins in a single transcript. A simple and effective artificial multi-hairpin method is identified here that stimulates production of mature 22-nucleotide small RNAs from modified miRNA hairpins, improves gene knockdown over single-hairpin constructs, and provides linked multi-gene knockdowns.

Introduction

A number of natural miRNA hairpins exist in clusters of multiple identical or different copies (Lagos-Quintana et al., 2001; Lau et al., 2001). This finding suggests that polycistronic transcripts might be naturally used to enhance the efficiencies of target gene repression or to achieve linked multi-gene repression. It is logical to hypothesize that polycistronic transcripts could be generated artificially to achieve better knockdown and linked multi-gene knockdown by modified miRNAs.

It was hypothesized that a second miRNA hairpin increases the production of miRNAs by additional mechanisms. Addition of a second miRNA hairpin within an appropriate distance from the first hairpin may stimulate processing of the two hairpins if this two-hairpin substrate is more efficiently recognized by the Drosha/DGCR8 micro-processor enzyme complex than a single hairpin substrate or an inappropriately spaced two-hairpin substrate. The Drosha/DGCR8 microprocessor enzyme complex has a molecular weight of 650 KDa and may contain two Drosha and DGCR8 subunits (Han et al., 2004; Grefory et al., 2004). This enzyme complex may therefore recognize a two-hairpin substrate more efficiently if the two hairpins are physically linked together by a distance similar to the dimensions of the Drosha/DGCR8 complex. In addition, processing of an appropriately spaced two-hairpin substrate can also be more efficient if the processing reaction is processive in which a second reaction taking place near the first reaction substrate is more likely to happen than starting a second reaction on a random new substrate.

We have now tested this hypothesis and discovered that the second hairpin could indeed stimulate processing when it is placed about 13 to 25 nucleotides away from the first hairpin. In this report, a simple multi-hairpin design is presented that effectively improves knockdown over single-hairpin constructs and provides linked multi-gene knockdowns.

Materials and Methods

Plasmid Construction. A previous protocol (Paddison et al., 2004) was followed, with modifications in PCR primer design, to construct the 118-nucleotide (nt) modified miR-30 hairpin (FIG. 1A) flanked by artificial sequences containing various restriction sites (FIG. 1B). PCR template and primer sequences are listed in Table 1.

TABLE 1

Sequences of PCR templates, primers, and hybridization probes

PCR Template Oligonucleotides[a]

| | |
|---|---|
| Skp2 P183088 | TGCTGTTGACAGTGAGCGAACCTTAGACC TCACAGGTAAATAGTGAAGCCACAGATGT ATTTACCTGTGAGGTCTAAGGTCTGCCTA CTGCCTCGGA (SEQ ID NO: 4) |
| AR HP140363 | TGCTGTTGACAGTGAGCGACCAGCAGAAA TGATTGCACTATAGTGAAGCCACAGATGT ATAGTGCAATCATTTCTGCTGGCTGCCTA CTGCCTCGGA (SEQ ID NO: 5) |
| Cyclin A HP105501 | TGCTGTTGACAGTGAGCGACGTTCCTCCT TGGAAAGCAAATAGTGAAGCCACAGATGT ATTTGCTTTCCAAGGAGGAACGGTGCCTA CTGCCTCGGA (SEQ ID NO: 6) |

TABLE 1-continued

Sequences of PCR templates, primers, and hybridization probes

PCR Primer Oligonucleotides[b]

| | |
|---|---|
| 5' primer | GCTXXXXXXGATCCAAGAAGGTATATTGC TGTTGACAGTGAGCG (SEQ ID NO: 7) |
| 3' primer | CTAXXXXXXXATCGTAGCCCTTGAAGTCCG AGGCAGTAGGCA (SEQ ID NO: 8) |

Hybridization Probes

| | |
|---|---|
| Skp2 target sense | CCTTAGACCTCACAGGTAA (SEQ ID NO: 9) |
| Skp2 target antisense | TTACCTGTGAGGTCTAAGG (SEQ ID NO: 10) |
| U6 antisense | GCAGGGGCCATGCTAATCTTCTCTGTATC G (SEQ ID NO: 11) |

[a]PCR template sequences containing specific target sequences were obtained from the RNAi Codex web site (codex.cshl.edu/scripts/newmain.pl). Bold letter sequences are derived from target genes. Note that the nucleotide at the 5' end of the sense sequence does not base pair with the nucleotide at the 3' end of the antisense sequence (see also FIG. 1A).
[b]PCR primer sequences contain desired restriction sequences represented by XXXXXX according to the cloning strategies shown in FIG. 1C. Bold letters represent artificial sequences.

The 97-nt template was amplified with VentR® DNA polymerase (New England Biolabs, Ipswich, Mass., USA) by 25 PCR cycles, each consisting of 30 s at 94° C., 30 s at 54° C., and 1 min at 75° C. Subsequently, 1 µL Taq DNA polymerase was added to the PCR product and incubated at 72° C. for 10 min. The PCR product was then cloned into pCR2.1-TOPO and confirmed by sequencing. Subsequent cloning steps are illustrated in FIG. 1C. Single- or multi-hairpin constructs were inserted into XbaI and BamHI sites of lenti-CMV-GFP (Fullenzi et al., 2002).

Cell Culture, Generation of Lentivirus, and Infection. 293T cells were cultured in Dulbecco's modified Eagle medium (DMEM) supplemented with 10% fetal bovine serum (FBS). Lentivirus were generated by cotransfecting 293T cells with various lentivirus plasmids and packaging plasmids (pM-DLg/pRRE, pRSV-REV, and pMD2-VSVG) (Fullenzi et al., 2002) by standard calcium phosphate protocol. After 48 h, supernatant was collected and filtered through a 0.2-µm filter. Virus titers were determined by infecting 293T cells with serial dilutions of virus stock and monitoring the percentage of green fluorescent protein (GFP) positive cells.

Northern Blot Analysis. Total RNA was extracted as described previously (Lagos-Quintana et al., 2001) and concentrated by precipitation with three volumes of ethanol. Thirty micrograms total RNA were fractionated on a 15% denaturing polyacrylamide gel, blotted in 0.5×Tris-borate-EDTA buffer (TBE; 1.35 M Tris base, 0.45 M boric acid, 0.02 M EDTA) onto a GeneScreen Plus® membrane (PerkinElmer Life and Analytical Sciences, Wellesley, Mass. USA), and hybridized in ULTRAhyb®-Oligo buffer (Ambion, Austin, Tex., USA). Ten femtomoles 19-nt antisense and sense oligonucleotides (Table 1) were also loaded to provide molecular weight and detection sensitivity references. The 19-nt sense oligonucleotides were end-labeled with T4 polynucleotide kinase (New England Biolabs). A U6 antisense oligonucleotide probe (Table 1) was used to probe for the 106-nt U6 RNA as control in the same Northern blot analysis. Total RNA was also fractionated on a 1.2% agarose/formaldehyde gel and blotted onto GeneScreen Plus membrane for analysis of large transcripts by hybridization in ULTRAhyb buffer to a randomly primed GFP or Skp2 cDNA fragment.

Western Blot Analysis. Cell lysates were prepared in lysis buffer [50 mM HEPES, pH 7.0, 250 mM NaCl, 0.1% Nonidet™ P40 (NP40), 5 mM EDTA, plus protease inhibitors]. Equal amounts of lysates (as determined by Bio-Rad Protein Assay Dye Reagent; Bio-Rad Laboratories, Hercules, Calif., USA) were loaded onto a 10% sodium dodecyl sulfate polyacrylamide gel electrophoresis (SDS-PAGE). Anti-Skp2 (Invitrogen, Carlsbad, Calif., USA), anti-AR, anti-Cdk2, and anti-Cyclin A (all from Santa Cruz Biotechnology, Santa Cruz, Calif., USA) were used as primary antibodies. Horseradish peroxidase (HRP)-conjugated secondary antibodies were used for detection by chemiluminescence.

Results and Discussion

For naturally occurring multi-miRNA hairpin clusters, it is not known whether any essential sequence elements are present in between the hairpins to ensure efficient processing of all hairpins in a transcript. For miR-30 however, detailed studies have shown that the pre-miR-30 hairpin can be generated correctly and efficiently in vitro when it is flanked by a minimum of 22 nt of its natural flanking sequences at its 5' side and 15 nt at its 3' side (Zeng and Cullen, 2005) (the bold-face letters in FIG. 1A). The importance of these flanking sequences lies in providing an extended imperfect short stem followed by several unpaired bases, rather than in providing specific sequence motifs (Zeng and Cullen, 2005; Lee et al., 2003). When the pre-miR-30 hairpin was embedded in arbitrary sequences of a longer transcript and expressed from a pol II promoter, flanking sequences that can provide a 5-bp extended stem have been found sufficient for its processing (Zeng et al., 2005), presumably because the arbitrary sequences outside the designed stem can provide unpaired bases. When expressed from a pol III promoter, however, processing of pre-miR-30 hairpins with approximately 10-20 nt natural flanking sequences was found to be inefficient in some studies (Zeng and Cullen, 2005; Chen et al., 2004). Inclusion of approximately 100 nt of natural flanking sequences on either side of the pre-miR-30 hairpin stimulated the production of mature miRNA from a pol III promoter (Chen et al., 2004), but knockdown efficiencies of the modified miR-30 hairpins flanked by approximately 125 nt of natural sequences were generally lower when expressed from pol III promoters compared with pol II promoters (Stegmeier et al., 2005; Dickens et al., 2005). These disadvantages of expressing miRNA from pol III promoters may reflect the fact that natural miRNAs are expressed from pol II promoters (Cai et al., 2004; Lee et al., 2004).

Based on these findings, an extended miR-30 hairpin of 118 nt was used as an expression unit for modified miR-30 hairpins (FIG. 1A) from a longer pol II transcript. It was reasoned that the addition of more natural flanking sequences onto the previously defined minimal flanking sequences should help ensure the presence of single-stranded extension in addition to the short-stem extension and therefore reduce the reliance on arbitrary flanking sequences. The expression units could then be linked with a short artificial sequence containing cloning sites (FIG. 1B). Two cloning strategies to build hairpin clusters were designed (FIG. 1C-E). Method A (FIG. 1E) can be Used to test the knockdown efficiency of a construct before adding progressively more hairpins, while Method B is better suited if one desires to start with a multi-hairpin construct. The hairpin or hairpin clusters were cloned into the XbaI and BamHI sites of a lentivirus vector about 70 nt downstream from a cytomegalovirus (CMV; i.e., promoter) and followed by a GFP open reading frame (ORF) to mark hairpin-expressing cells (FIG. 1F). Lentiviruses can achieve high efficiency gene transduction in both dividing and quiescent cells.

To test the multi-hairpin method, lenti-CMV-miSkp2-GFP (miSkp2 indicates miRNA hairpin targeting Skp2), lenti-CMV-miSkp2-miSkp2-GFP, and lenti-CMV-miSkp2-miSkp2-miSkp2-GFP were constructed to perform knockdown of cellular Skp2. 293T cells were infected with these lenti-viruses at approximately 30% efficiency, so that transduced cells should contain similarly low numbers of the vectors.

When analyzing transduced cells for GFP expression, a clear inverse relationship between the intensity of GFP fluorescence and hairpin copy numbers was observed (FIGS. 2A and B). Since processing of hairpins would lead to-destruction of the primary transcript from which GFP is translated, this inverse relationship may suggest that the multi-hairpin transcripts were processed more efficiently than the single-hairpin transcript. GFP positive (regardless of green fluorescence intensity) cells were separated from negative cells by flow cytometry and the levels and status of GFP transcripts was determined by Northern blot analysis. As shown in FIG. 2C, the addition of one, two, and three hairpins to the GFP-expressing transcript led to the corresponding increases in transcript sizes as expected. The amounts of one-, two-, and three-hairpin transcripts were all significantly reduced compared with the amount of the hairpin-less GFP transcript. The most notable difference between single-hairpin transcript and two- or three-hairpin transcripts is that the single-hairpin transcript still retained a relatively intact size, while transcripts from two- and three-hairpin vectors showed extensive downward smearing, consistent with more efficient processing of the multi-hairpins. However, these results cannot rule out the possibility that presence of increasing numbers of hairpins could also inhibit translation of the downstream GFP ORF.

Next, the production of Skp2-specific 22-nt small RNAs from various hairpin constructs was determined and compared by Northern blot analysis of total RNAs isolated from GFP positive cells. As shown in FIG. 2D, the addition of the second hairpin led to a large increase in the amount of 22-nt small RNAs. complementary to the sense strand of the stem of the miSkp2 hairpin. Addition of the third hairpin further generated more 22-nt small RNAs, but the increase was not as intense as the gain observed with the two-hairpin construct over the single-hairpin construct. Consistent with a number of previous reports (see Silva et al., 2005 for example), no significant accumulation of pre-miRNAs of 60-70 nt was observed in cells transduced with our single- and multi-hairpin constructs (data not shown), suggesting that processing of pre-miRNA by Dicer is very efficient and not rate-limiting in this experimental setting. Importantly, the degree of improvement achieved by the two-hairpin construct over the single-hairpin construct is clearly disproportionably larger than the one-fold increase in hairpin copy number, suggesting that the addition of a second hairpin according to our design provided robust stimulation to the miRNA processing process.

Figure 3:
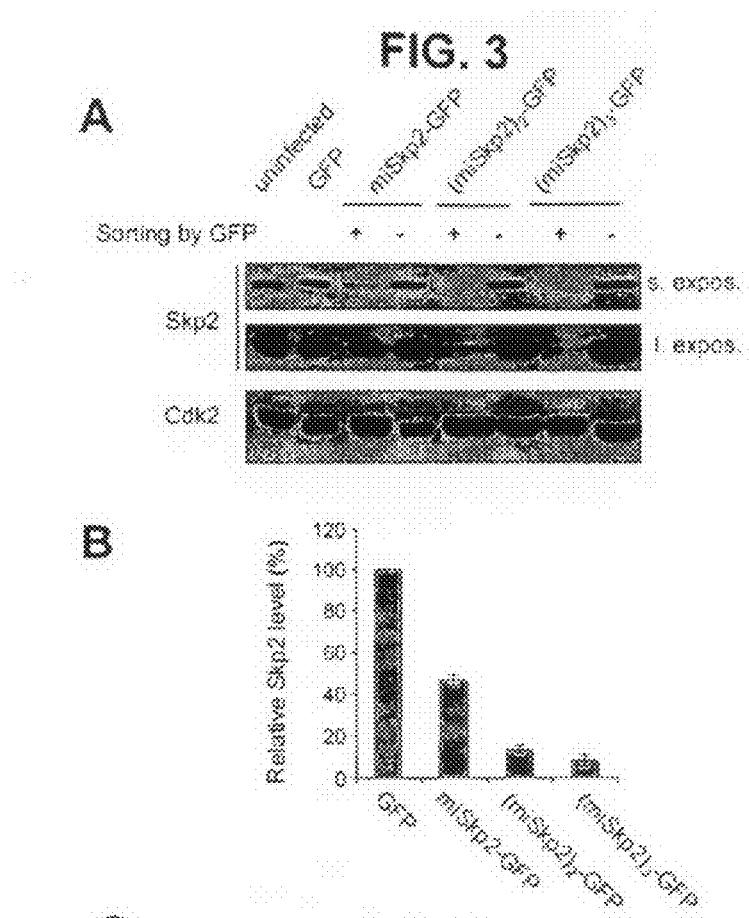
FIG. 3 shows photographs of blots and a graph showing improved knockdown by multi-microRNA (miRNA) hairpin vectors. Panel A shows a western blot analysis of 293T cells infected at approximately 30% efficiency for 4 days by the indicated viruses, then sorted by flow cytometry to separate green fluorescent protein (GFP) positive and negative cells, which were subjected to western blot with the indicated antibodies. The anti-Skp2 blot was exposed for approximately 10 s (short exposure) and approximately 60 s (long exposure). Panel B is a graph of the results from three experiments similar to the one shown in panel A. Panel C shows a northern blot analysis of total RNAs isolated from GFP positive cells transduced with the indicated lentiviruses. The membrane from the experiment shown in FIG. 2C was stripped and reprobed with a Skp2 cDNA probe. Panel D shows a western blot analysis of LNCaP cells infected at >95% efficiency by the indicated viruses for 4 days, then harvested and subjected to western blot with the indicated antibodies.

The knockdown efficiencies of various hairpin constructs was next determined by western blotting for endogenous Skp2 in GFP positive and negative cells (FIG. 3A). At non-saturating levels of exposure, Skp2 western blot analysis shows reasonably good knockdown of Skp2 by lenti-CMV-miSkp2-GFP. Upon longer exposure, a substantial amount of Skp2 protein was revealed in cells transduced with lenti-CMV-miSkp2-GFP. At this level of detection, it is clear that addition of a second miSkp2 hairpin led to significant and consistent improvement of knockdown in multiple experiments (FIG. 3B). Addition of the third miSkp2 hairpin further reduced Skp2 protein levels, although accurate quantification was difficult since Skp2 protein levels were already very low in cells transduced with the two-hairpin construct.

The extent of knockdown at the levels of cellular Skp2 mRNA was also determined. The Northern blot analysis shown in FIG. 3C demonstrates that while the single-hairpin construct achieved significant knockdown, Skp2 transcript levels were further reduced to below the levels of detection by the addition of the second hairpin.

This method was used to knockdown another cellular gene, the androgen receptor (AR), in another cell line, LNCaP, a the prostate cancer cell line). See FIG. 3D. In this experiment, LNCaP cells were infected at >95% efficiency. Knockdown by the single-hairpin construct was already very efficient, but addition of the second hairpin clearly further improved knockdown. In scenarios like this, it was decided not to continue with adding the third hairpin. It was concluded that, except for certain single-hairpin-vectors that can already achieve near-complete knockdowns when expressed from low numbers of knockdown vectors, the described multi-hairpin method should be broadly and immediately applicable when knockdown by a single-hairpin construct leaves room for varying degrees of improvement.

The above findings, that the addition of a second hairpin provided disproportionably large increases in mature small RNA production and gene knockdown efficiency, led to the determination of whether addition of a different irrelevant hairpin could similarly improve Skp2 knockdown by a single miSkp2 hairpin Lenti-CMV-miAR-miSkp2-GFP was constructed, in which miAR serves as an irrelevant hairpin, since 293T cells do not express the AR and lenti-CMV-miAR-GFP did not alter Skp2 levels in 293T cells (FIG. 4A, top). As shown in FIG. 4A, bottom, Skp2 knockdown efficiency of lenti-CMV-miAR-miSkp2-GFP is much closer to that of lenti-CMV-miSkp2-miSkp2-GFP than to CMV-miSkp2-GFP. These results demonstrate that knockdown efficiency of a single hairpin can be significantly improved by the presence of a second hairpin even when it does not target the same gene.

It was next determined whether the second hairpin in the two-hairpin construct could also affect effective gene knockdown. If this were the case, it would be predicted that our multi-hairpin design could be used to knockdown more than one gene in a linked fashion. Lenti-CMV-miCycA-miSkp2-GFP was constructed to test whether this two-hairpin construct can knockdown cyclin A and Skp2 at the same time. As shown in FIG. 4B, knockdown of Skp2 by lenti-CMV-miSkp2-GFP did not affect levels of cyclin A (lane 2), while knockdown of cyclin A caused a small decrease in Skp2 protein levels (lane 3). The latter result may reveal a hitherto unknown dependence of Skp2 protein levels on cyclin A. On this basis, lenti-CMV-miCycA-miSkp2-GFP showed the ability to knockdown both cyclin A and Skp2 at a higher efficiency than the respective single-hairpin vectors (lane 4), suggesting that both hairpins in the two-hairpin construct are functionally active. We further show that lenti-CMV-miCycA-miSkp2-GFP and lenti-CMV-miSkp2-miCycA-GFP affected similar knockdowns of cyclin A and Skp2 (lanes 4 and 5), indicating that the relative position of a hairpin in the two-hairpin cluster is flexible. Whether the third hairpin in our multi-hairpin design can achieve effective knockdown of a third gene remains to be determined with the appropriate cellular genes that are not dependent on each other.

In summary, a method is presented for applying the multi-hairpin feature found in natural miRNA to artificially modified miR-30. With this method, knockdown efficiencies of single-hairpin constructs can be significantly improved, and at least two genes can be knocked down in a linked fashion. These features of this method should improve the use of gene knockdown in laboratory research and facilitate the development of more efficacious gene silencing-based therapeutics. Further studies on the strong stimulatory effects of our multi-hairpin design on the production of mature miRNAs should provide new insight into the mechanisms of miRNA processing.

EXAMPLE 2

Optimization of Distance Between miRNA-30 Hairpins

If the net effect of expressing two identical hairpins in a single transcript is to provide a two-fold increase in the amount of the microRNA hairpin for processing, such a strategy would be expected to yield a two-fold increase in the production of mature microRNA and a similar degree of improvement of gene knockdown.

It is hypothesized here that a certain degree of synergistic processing could be triggered by placing the two microRNA hairpins close together, at an appropriate distance. The first step in the processing of microRNA hairpins is excision at the base of the stem of the microRNA hairpin by the Drosha/DGCR8 complex. It is hypothesized that when two microRNA hairpins are closely placed in a single transcript with an appropriate distance, the processing of one microRNA hairpin could facilitate the processing of the adjacent hairpin with a synergistic mechanism. This could be achieved if the processing reaction is processive in which a second reaction taking place near the first reaction substrate is more likely to happen than starting a second reaction on a random new substrate. It is also possible that the Drosha/DGCR8 complex may have more than one enzymatic processing centers, and could recruit two appropriately spaced microRNA hairpins more efficiently than a single-hairpin substrate or a two-hairpin substrate in which the two hairpins are spaced father away.

Figure 5:
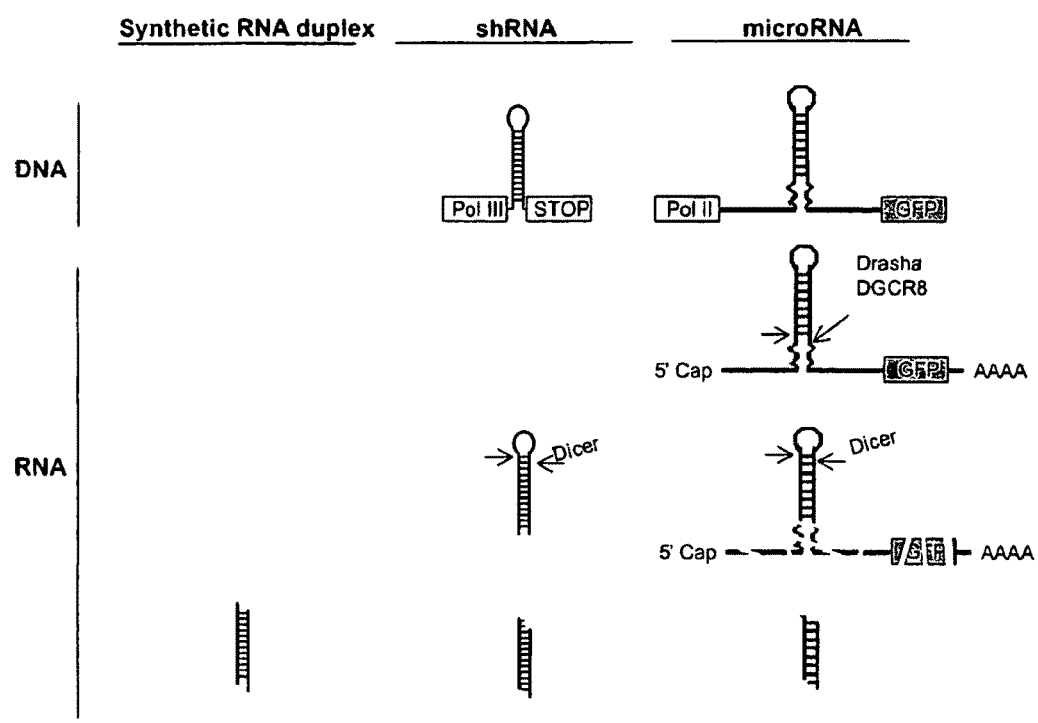
FIG. 5 is a diagram illustrating the use of the GFP gene to assess miRNA processing efficiency.

It has been established in previous studies that microRNA hairpins could be expressed from RNA polymerase II (pol II) transcripts that also encode an open reading frame such as the GFP protein. Here, this property was used as a quantitative measurement of the efficiency of the processing of microRNA by the Drosha/DGCR8 complex, since processing by Drosha/DGCR8 would lead to the subsequent degradation of the transcript encoding GFP (FIG. 5). The levels of GFP in cells can be accurately measured by flow cytometry analysis.

Figure 6:
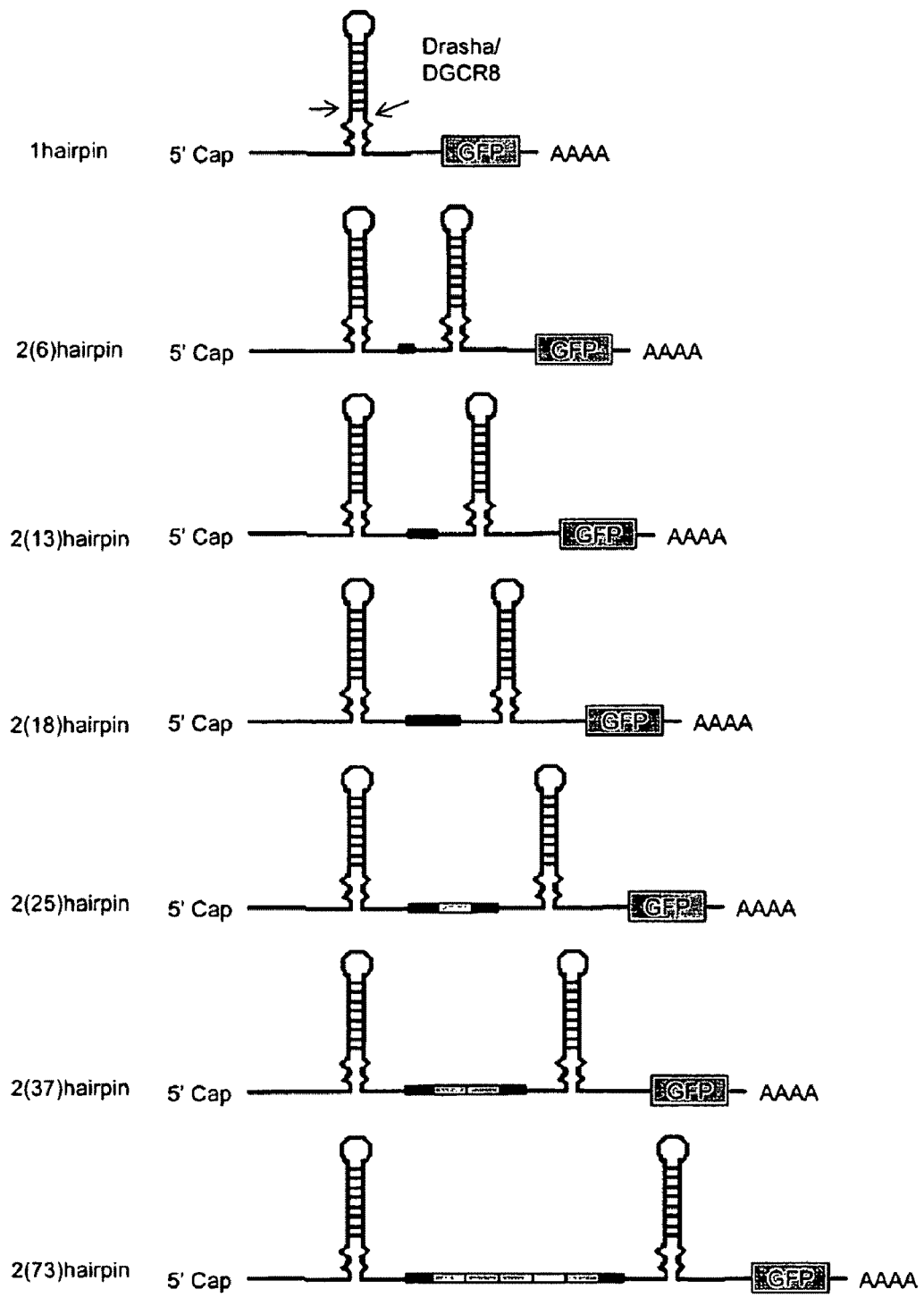
FIG. 6 is diagrams illustrating the miRNA-GFP constructs used to determine the effect of distance between miRNA precursors on processing efficiency.

A series of two hairpin-expressing constructs was constructed, as illustrated in FIG. 6. The only differences among these constructs arc the number of RNA bases between the two neighboring microRNA hairpins, which ranges from 6 nt to 73 nt. The exact space sequences of the constructs are shown in FIG. 8A. The ATG sequence was avoided to prevent undesired initiation of translation. Longer spacing sequences contained multiple copies of the same sequences in the shorter spacing sequences to minimize the possibility of introducing sequences that could affect processing of hairpins when the spacing increases.

Figure 7:
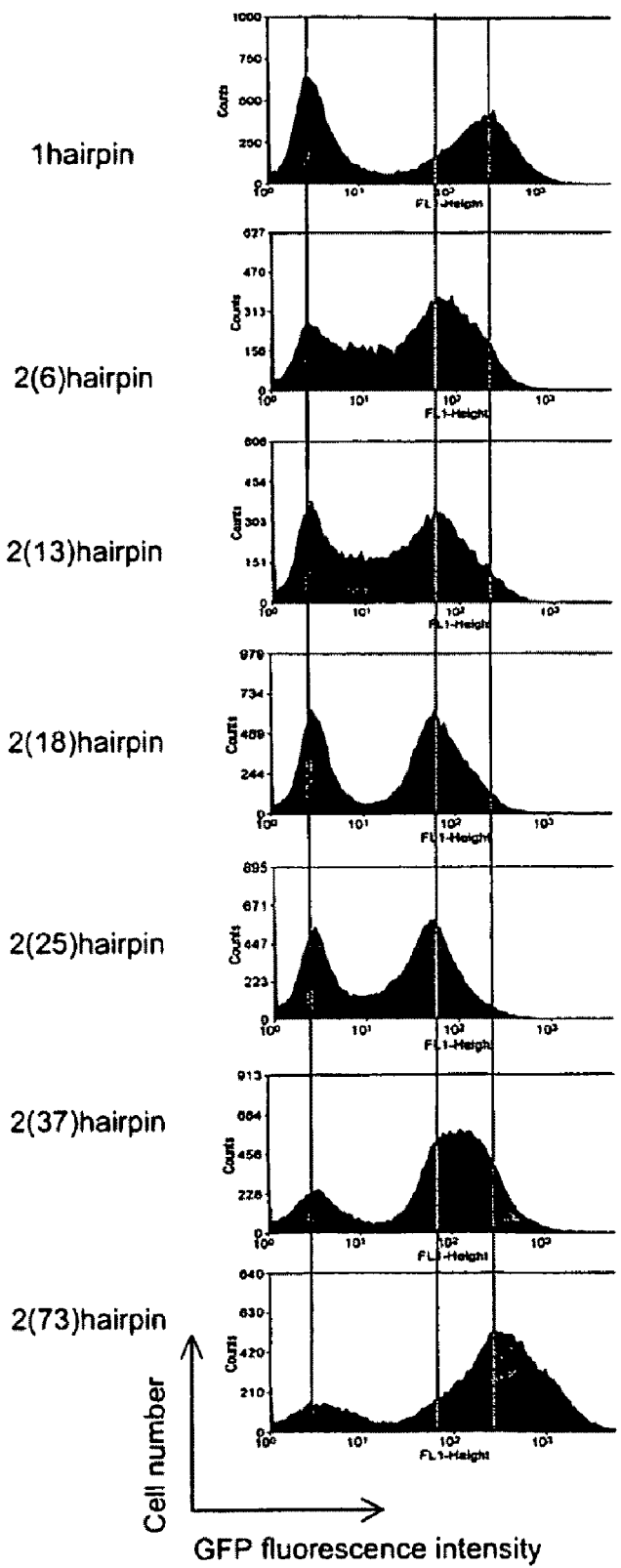
FIG. 7 is graphs of flow cytometry analysis showing GFP levels in cells following processing of the various miRNA-GFP constructs illustrated in FIG. 6.

These transcripts were expressed from a CMV promoter in a lentivirus vector as in Example 1 (FIG. 1D). The human 293T cells were transduced at about 50% efficiency and the GFP expression profiles were determined by flow cytometry. Results are provided in FIG. 7. These results show that the GFP expression levels were the same in cells transduced with a one-hairpin lentivirus and in cells transduced with a two-hairpin lentivirus in which the two hairpins were spaced 73-nt apart (the 2(73)hairpin). This finding suggests that processing efficiencies of the one-hairpin transcript and this two-hairpin transcript were similar. The 2-fold increase in hairpin copy number did not result in more efficient processing of the transcript. However, GFP expression was significantly reduced (about 5-fold) in cells expressing the 2(13)hairpin, 2(18)hairpin, or 2(25)hairpin, suggesting that spacing the two microRNA hairpins closer together at these distances led to synergistic increases in the efficiency of processing of these transcripts. A reduction of the spacing to 6 nt (the 2(6)hairpin)), or an increase of the spacing to 37 nt (the 2(37)hairpin) led to clear increases in GFP expression levels. These results reveal that two closely linked microRNA hairpin units could indeed induce synergistic processing. The optimal spacing between the two microRNA hairpins is 13 to 25 nt. When the spacing distance between the two linked microRNA hairpins is longer than 70 nt, this synergistic effect becomes insignificant.

Physical dimensions of various spacing lengths and the Drasha/DGCR8 complex were calculated. The average distance between two consecutive phosphate groups alone the RNA backbone is about 5.9 Å (Hyeon et al., 2006). Based on this characteristic of RNA, spacing lengths of various two-hairpin constructs were calculated and shown in FIG. 8A. The Drosha/DGCR8 micro-processor enzyme complex (FIG. 8C) was determined to have a molecular weight of about 650 KDa based on gel filtration chromatography (Han et al., 2004; Grefory et al., 2004), which means $650 \times 10^3$ g/mole. This number was divided by Avocado's constant $6.02 \times 10^{23}$ to get the mass of a single complex of $1.08 \times 10^{-18}$ g/molecule. Assuming the density of the protein complex is close to that of the water (1 g/cm$^3$), the size of one Drasha/DGCR8 complex would be $1.08 \times 10^{-18}$ cm$^3$, or $1.08 \times 10^{-24}$ m$^3$. Assuming that the Drosha/DGCR8 complex has the shape of a ball, the radius of the complex can be calculated by the equation $4/3\pi r^3 = 1.08 \times 10^{-24}$ m$^3$. Result of this calculation is $0.63 \times 10^{-8}$ m$^3$, or 63 Å. The diameter of the Drosha/DGCR8 complex therefore is about 126 Å. These calculations reveal that the diameter of the Drasha/DGCR8 complex, 126 Å, fits in the center of the optimal spacing distance of 77 Å to 148 Å (FIG. 8C).

The experimental data and calculations led to a proposed model for the synergistic processing of two-hairpin-constructs. In this model, when two linked hairpins are spaced at distances that roughly equal the diameter of the Drosha/DGCR8 complex, they represent the best substrate for recognition and binding by the Drosha/DGCR8 complex. Since the Drosha/DGCR8 complex contains two units of Drosha and DGCR8 proteins (Han et al., 2004), once such two-hairpin construct is bound by the Drosha/DGCR8 complex, the two hairpins may be processed simultaneously or processively. Combination of these two synergistic steps lead to increases in processing efficiencies that are significantly greater than the two-fold increase in miRNA hairpin copy numbers.

REFERENCES

Boden, D., O. Pusch, R. Silbermann, F. Lee, L. Tucker, and B. Ramratnam. 2004. Enhanced gene silencing of HIV-1 specific siRNA using microRNA designed hairpins. Nucleic Acids Res. 32:1154-1158.

Cai, X., C. H. Hagedorn, and B. R. Cullen. 2004. Human microRNAs are processed from capped, polyadenylated transcripts that can also function as mRNAs. RNA 10:1957-1966.

Chen, C. Z., L. Li, H. F. Lodish, and D. P. Bartel. 2004. MicroRNAs modulate hematopoietic lineage differentiation. Science 303:83-86.

Dickins, R. A., M. T. Hemann, J. T. Zilfou, D. R. Simpson, I. Ibarra, G. J. Hannon, and S. W. Lowe. 2005. Probing tumor phenotypes using stable and regulated synthetic microRNA precursors. Nat. Genet. 37:1289-1295.

Follenzi, A., G. Sabatino, A. Lombardo, C. Boccaccio, and L. Naldini. 2002. Efficient gene delivery and targeted expression to hepatocytes in vivo by improved lentiviral vectors. Hum. Gene Ther. 13:243-260.

Grefory R L, Yan K P, Amuthan G, Chendrimada T, Doratotaj B, Cooch N, Shiekhattar R. 2004. The Microprocessor complex mediates the genesis of microRNAs. Nature 432:235-40

Han J, Lee Y, Yeom K H, Kim Y K, Jin H, Kim V N. 2004. The Drosha-DGCR8 complex in primary microRNA processing. Genes Dev. 18:3016-27.

Hyeon, C., Dima, R. I., and Thirumalai, D. 2006. Size, shape, and flexibility of RNA structure. J Chem Phys 125:194905.

Kim, V. N. 2005. Nature Reviews: Molecular and Cellular Biology 6:376-385.

Lagos-Quintana, M., R. Rauhut, W. Lendeckel, and T. Tuschl. 2001. Identification of novel genes coding for small expressed RNAs. Science 294:853-858.

Lau, N. C., L. P. Lim, E. G. Weinstein, and D. P. Bartel. 2001. An abundant class of tiny RNAs with probable regulatory roles in Caenorhabditis elegans. Science 294:858-862.

Lee, Y., C. Ahn, J. Han, H. Choi, J. Kim, J. Yim, J. Lee, P. Provost, et al. 2003. The nuclear RNase III Drosha initiates microRNA processing. Nature 425:415-419.

Lee, Y., M. Kim, J. Han, K. H. Yeom, S. Lee, S. H. Baek, and V. N. Kim. 2004. MicroRNA genes are transcribed by RNA polymerase II. EMBO J. 23:4051-4060.

McManus, M. T., C. P. Petersen, B. B. Haines, J. Chen, and P. A. Sharp. 2002. Gene silencing using micro-RNA designed hairpins. RNA 8:842-850.

Paddison, P. J., M. Cleary, J. M. Silva, K. Chang, N. Sheth, R. Sachidanandam, and G. J. Hannon. 2004. Cloning of short hairpin RNAs for gene knockdown in mammalian cells. Nat. Methods 1: 163-167.

Silva, J. M., M. Z. Li, K. Chang, W. Ge, M. C. Golding, R. J. Rickles, D. Siolas, G. Hu, et al. 2005. Second-generation shRNA libraries covering the mouse and human genomes. Nat. Genet. 37:1281-1288.

Stegmeier, F., G. Hu, R. J. Rickles, G. J. Hannon, and S. J. Elledge. 2005. A lentiviral microRNA-based system for single-copy polymerase II-regulated RNA interference in mammalian cells. Proc. Natl. Acad. Sci. USA 102:13212-13217.

Zeng, Y. and B. R. Cullen. 2003. Sequence requirements for micro RNA processing and function in human cells. RNA 9:112-123.

Zeng, Y. and B. R. Cullen. 2005. Efficient processing of primary microRNA hairpins by Drosha requires flanking nonstructured RNA sequences. J. Biol. Chem. 280:27595-27603.

Zeng, Y., E. J. Wagner, and B. R. Cullen. 2002. Both natural and designed micro RNAs can inhibit the expression of cognate mRNAs when expressed in human cells. Mol. Cell 9:1327-1333.

Zeng, Y., X. Cai, and B. R. Cullen. 2005. Use of RNA polymerase II to transcribe artificial microRNAs. Methods Enzymol. 392:371-380.

Zhou, H., X. G. Xia, and Z. Xu. 2005. An RNA polymerase II construct synthesizes short-hairpin RNA with a quantitative indicator and mediates highly efficient RNAi. Nucleic Acids Res. 33:e62.

United States Patent Application Publication No. US 2004/0053411 A1.

United States Patent Application Publication No. US 2006/0063174 A1.

PCT Publication No. WO 2006/044322 A2.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

Appendix—SEQ ID NOs

Curly brackets indicate optional ribonucleotides; square brackets delineate alternative sequences; (X/Y)=either X or Y at that position; $N(a)_{20-22}$ and $N(b)_{22}$=20-22 nucleotides complementary to target sequence, where the (a) sequence and the (b) sequence base pair to each other in the stem of the hairpin.

SEQ ID NO: 1
GACAGUGAGCGNN ($N_{20-22}$) {UA}[GUGA(A/G)(G/A)C(C/G)(A/C)(C/G) or ACAGCG](A/U)GA(U/G)(G/A)UG{UG} ($N_{20-22}$) UGCCUACUGC CUCGG

SEQ ID NO: 2
GACAGUGAGCGNN ($N_{20}$) GUGA(A/G)(G/A)C(C/G)(A/C)(C/G)(A/U)GA(U/G)(G/A)UG ($N_{20}$) UGCCUACUGC CUCGG

SEQ ID NO: 3
AAGAAGGUAU AUUGCUGUUG ACAGUGAGCGNN ($N_{20}$) UAGUGAAGCCACAGAUGUA ($N_{22}$) UGCCUACUGC CUCGGACUUC AAGGG

SEQ ID NO: 4 - Skp2 P183088 PCR template oligonucleotide
TGCTGTTGACAGTGAGCGAACCTTAGACCTCACAGGTAAATAGTGAAGCC ACAGATGTATTTACCTGTGAGGTCTAAGGTCTGCCTACTGCCTCGGA SEQ ID NO: 5 - AR HP140363 PCR template oligonucleotide
TGCTGTTGACAGTGAGCGACCAGCAGAAATGATTGCACTATAGTGAAGCC ACAGATGTATAGTGCAATCATTTCTGCTGGCTGCCTACTGCCTCGGA SEQ ID NO: 6 - Cyclin A HP105501 PCR template oligonucleotide
TGCTGTTGACAGTGAGCGACGTTCCTCCTTGGAAAGCAAATAGTGAAGCC ACAGATGTATTTGCTTTCCAAGGAGGAACGGTGCCTACTGCCTCGGA SEQ ID NO: 7 - 5' primer for PCR
GCTXXXXXXGATCCAAGAAGGTATATTGCTGTTGACAGTGAGCG SEQ ID NO: 8 - 3' primer for PCR
CTAXXXXXXXATCGTAGCCCTTGAAGTCCGAGGCAGTAGGCA SEQ ID NO: 9 - Skp2 target sense hybridization probe
CCTTAGACCTCACAGGTAA SEQ ID NO: 10 - Skp2 target antisense hybridization probe
TTACCTGTGAGGTCTAAGG SEQ ID NO: 11 - U6 antisense hybridization probe
GCAGGGGCCATGCTAATCTTCTCTGTATCG

What is claimed is:

1. A DNA comprising a polynucleotide that encodes at east a first modified miR-30 precursor and a second modified miR-30 precursor,
    wherein the first and second modified miR-30 precursors are each at least 80 nucleotides long and comprise a stem-loop structure,
    wherein the first modified miR-30 precursor further comprises a first miRNA sequence of 20-22 nucleotides on the stem of the stem-loop structure complementary to a portion of a first target sequence wherein the first target sequence is a first naturally occurring mRNA sequence,
    wherein the second modified miR-30 precursor further comprises a second miRNA sequence of 20-22 nucleotides on the stem-loop structure complementary to a second target sequence, and
    wherein the first and second modified miR-30 precursors each independently further comprise a sequence complementary to the first and second miRNA sequence of 20-22 nucleotides, respectively, that base-pairs to the first and second miRNA sequence of 20-22 nucleotides, respectively, in the stem of the stem-loop structure, and wherein the first modified miR-30 precursor and the second modified miR-30 precursor are 13-25 nucleotides apart.

2. The DNA of claim 1, wherein the first target sequence is the same as the second target sequence.

3. The DNA of claim 1, wherein the first target sequence and he second target sequence are on the same mRNA or on different mRNAs.

4. The DNA of claim 1, wherein the second target sequence does not natural y occur in the same species as the first target sequence.

5. The DNA of claim 1, wherein the second target sequence naturally occurs in the same species as the first target sequence.

6. The DNA of claim 1, wherein the modified miR-30 comprises SEQ ID NO:1.

7. The DNA of claim 1, wherein the modified miR-30 comprises SEQ ID NO:2.

8. The DNA of claim 1, wherein the modified miR-30 comprises SEQ ID NO:3.

9. The DNA of claim 1, wherein the first target sequence and/or the second target sequence is complementary to a DNA from a mammalian pathogen.

10. The DNA of claim 9, wherein the mammalian pathogen is a human pathogen.

11. The DNA of claim 9, wherein the mammalian pathogen is a virus.

12. The DNA of claim 1, wherein the first target sequence and/or the second target sequence is complementary to a mammalian DNA.

13. The DNA of claim 12, wherein the mammalian mRNA is a human mRNA.

14. The DNA of claim 12, wherein the mammalian mRNA encodes an enzyme.

15. The DNA of claim 14, wherein the enzyme is a kinase or phosphatase.

16. The DNA of claim 12, wherein the mammalian mRNA encodes a skp2 protein.

17. The DNA of claim 12, wherein the mammalian mRNA encodes a receptor.

18. The DNA of claim 1, wherein the first and second modified miR-30 precursors are each at least 85 nucleotides long.

19. The DNA of claim 1, wherein the first and second modified miR-30 precursors are each 80-150 nucleotides long.

20. The DNA of claim 1, further comprising a; site for a restriction endonuclease between the firs modified miR-30 precursor and the second modified miR-30 precursor.

21. The DNA of claim 1, further comprising a promoter operably linked to the isolated DNA such that, when introduced into a eukaryotic cell, the first miR-30 precursor is transcribed and processed into the first miRNA and the second miR-30 precursor is transcribed and processed into the second miRNA.

22. The DNA of claim 21, wherein the promoter is a mammalian promoter.

23. The DNA of claim 21, wherein expression of a polypeptide encoded by the first naturally occurring mRNA sequence is reduced in the eukaryotic cell after the isolated DNA is introduced into the eukaryotic cell.

24. The DNA of claim 1, further comprising a gene encoding a detectable moiety.

25. The DNA of claim 24, wherein the gene encoding a detectable moiety encodes a green fluorescent protein (GFP).

26. The DNA of claim 1, wherein
    the first and second modified miR-30 precursors are each about 118 nucleotides long;
    the first modified miR-30 precursor and the second modified miR-30 precursor are about 18 nucleotides apart;
    the DNA further comprises a site for a restriction endonuclease between the first modified miR-30 precursor and the second modified miR-30 precursor;
    the DNA further comprises a gene encoding a encodes a green fluorescent protein (GFP); and
    the DNA further comprises a promoter operably linked to the isolated DNA such that, when introduced into a eukaryotic cell, the first miR-30 precursor is transcribed and processed into the first miRNA and the second miR-30 precursor is transcribed and processed into the second miRNA, wherein the promoter is a cytomegalovirus promoter.

27. The DNA of claim 26, wherein the first target sequence and/or the second target sequence is complementary to a mammalian mRNA encoding a skp2 protein.

28. A eukaryotic cell comprising the DNA of claim 21.

29. A vector comprising the DNA of claim 21, wherein the vector can replicate in a host cell.

30. A lentiviral vector comprising the isolated DNA of claim 26.

31. A mammalian cell transfected with the lentiviral vector of claim 30.

32. A method of inhibiting expression of a target gene in a eukaryotic cell, the method comprising introducing into the eukaryotic cell a DNA comprising a polynucleotide that encodes at least a first modified miR-30 precursor and a second modified miR-30 precursor,
- wherein the first and second modified miR-30 precursors are each at least 80 nucleotides long and comprise a stem-loop structure,
- wherein the first modified miR-30 precursor further comprises a first miRNA sequence of 20-22 nucleotides on the stem of the stem-loop structure complementary to a portion of a first target sequence, wherein the first target sequence is the mRNA of the target gene,
- wherein the second modified miR-30 precursor further comprises a second miRNA sequence of 20-22 nucleotides on the stem-loop structure complementary to a second, target sequence,
- wherein the first and second modified miR-30 precursors each independently further comprise a sequence complementary to the first and second miRNA sequence of 20-22 nucleotides, respectively, that base-pairs to the first and second miRNA sequence of 20-22 nucleotides, respectively, in the miR-30 precursor in the stem of the stem-loop structure,
- wherein the first modified miR-30 precursor and the second modified miR-30 precursor are 13-25 nucleotides apart, and
- wherein the DNA further comprises a promoter operably linked to the DNA such that, when the DNA is introduced into the eukaryotic cell, the first miR-30 precursor is transcribed and processed into the first miRNA and the second miR-30 precursor is transcribed and processed into the second miRNA, so as to thereby inhibit expression of the target gene in the eukaryotic cell.

* * * * *